(12) United States Patent
Harada et al.

(10) Patent No.: US 7,622,553 B2
(45) Date of Patent: Nov. 24, 2009

(54) RHESUS MONKEY DICKKOPF-1, NUCLEOTIDES ENCODING SAME, AND USES THEREOF

(75) Inventors: Shun-ichi Harada, Ambler, PA (US); Viera Kasparcova, Collegeville, PA (US); Helmut Glantschnig, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 213 days.

(21) Appl. No.: 10/579,605

(22) PCT Filed: Nov. 12, 2004

(86) PCT No.: PCT/US2004/038489

§ 371 (c)(1), (2), (4) Date: May 17, 2006

(87) PCT Pub. No.: WO2005/049640

PCT Pub. Date: Jun. 2, 2005

(65) Prior Publication Data

US 2007/0111253 A1  May 17, 2007

Related U.S. Application Data

(60) Provisional application No. 60/520,708, filed on Nov. 17, 2003.

(51) Int. Cl.
  *C07K 14/00* (2006.01)
  *C07K 17/00* (2006.01)
  *G01N 33/53* (2006.01)
(52) U.S. Cl. ........................ 530/350; 435/7.2
(58) Field of Classification Search .................. None
  See application file for complete search history.

(56) References Cited

U.S. PATENT DOCUMENTS

| | | | |
|---|---|---|---|
| 7,057,017 B2 * | 6/2006 | McCarthy | 530/350 |
| 2003/0068312 A1 | 4/2003 | McCarthy | |
| 2003/0181660 A1 | 9/2003 | Todd et al. | |
| 2004/0038860 A1 * | 2/2004 | Allen et al. | 514/2 |
| 2005/0069915 A1 | 3/2005 | McCarthy | |
| 2005/0079173 A1 | 4/2005 | Niehrs et al. | |
| 2005/0244826 A1 * | 11/2005 | Niehrs et al. | 435/6 |

FOREIGN PATENT DOCUMENTS

| | | |
|---|---|---|
| WO | WO 98/46743 | 10/1998 |
| WO | WO 98/46755 | 10/1998 |
| WO | WO 99/22000 | 5/1999 |
| WO | WO 00/52047 | 9/2000 |
| WO | WO 02/092015 | 11/2002 |
| WO | WO02092015 | * 11/2002 |

OTHER PUBLICATIONS

Bafico et al., Nature Cell Biology, vol. 3 (2001), pp. 683-686, "Novel mechanism of Wnt signalling inhibition mediated by Dickkopf-1 interaction with LRP6/Arrow".
Bennett et al., J. of Biol. Chem., vol. 277 (2002), pp. 30998-31004, "Regulation of Wnt signaling during adipogenesis".
Boyden et al., N. Eng. J. of Med., vol. 346 (2002), pp. 1513-1521, "High bone density due to a mutation in LDL-receptor-related protein 5".
Davidson et al,. Development, vol. 129 (2002), pp. 5587-5596, "Kremen proteins interact with Dickkopf1 to regulate anteroposterior CNS patterning".
Fujino et al., PNAS, vol. 100 (2003), pp. 229-234, "Low-density lipoprotein receptor-related protein 5 (LRP5) is essential for normal cholesterol metabolism and glucose-induced insulin secretion".
Glinka et al., Nature, vol. 391 (1998), pp. 357-362, "Dickkopf-1 is a member of a new family of secreted proteins and functions in head induction".
Gong et al., Cell, vol. 107 (2001), pp. 513-523, "LDL receptor-related protein 5 (LRP5) affects bone accrual and eye development".
Hey et al., Gene, vol. 216 (1998), pp. 103-111, "Cloning of a novel member of the low-density lipoprotein receptor family".
Hsu et al., Molecular and Cellular Biol., vol. 18 (1998), pp. 4807-4818, "Modulation of transcriptional regulation by LEF-1 in response to Wnt-1 signaling and association with beta-catenin".
Katagiri et al., J. of Cell Biology, vol. 127 (1994), pp. 1755-1766, "Bone morphogenetic protein-2 converts the differentiation pathway of C2C12 myoblasts into the osteoblast lineage".
Kato et al., J. of Cell Biology, vol. 157 (2002), pp. 303-314, "Cbfa1-independent decrease in osteoblast proliferation, osteopenia, and persistent embryonic eye vascularization in mice deficient in Lrp5, a Wnt coreceptor".
Krupnik et al., Gene, vol. 238 (1999), pp. 301-313, "Functional and structural diversity of the human Dickkopf gene family".
Li et al., The EMBO Journal, vol. 18 (1999), pp. 4233-4240, "Axin and Frat1 interact with Dvl and GSK, bridging Dvl to GSK in Wnt-mediated regulation of LEF-1".

(Continued)

*Primary Examiner*—Daniel C Gamett
(74) *Attorney, Agent, or Firm*—Patricia L. Chisholm; Valerie J. Camara

(57) ABSTRACT

The present invention provides rhesus monkey dickkopf-1 (rhDkk-1) and nucleotide sequences encoding it. Also provided herein are recombinant vectors, and recombinant hosts comprising rhDkk-1-encoding nucleotide sequences. Isolated rhDkk-1 can be used to screen and identify novel osteoanabolic compounds that stimulate bone formation for the treatment of osteoporosis or other disorders characterized by insufficient bone mass.

6 Claims, 7 Drawing Sheets

OTHER PUBLICATIONS

Little et al., Am. J. Hum. Genet., vol. 70 (2002), pp. 11-19, "A mutation in the LDL receptor-related protein 5 gene results in the autosomal dominant high-bone-mass trait".

Magoori et al, J. of Biol. Chem., vol. 278 (2003), pp. 11331-11336, "Severe hypercholesterolemia, impaired fat tolerance, and advanced atherosclerosis in mice lacking both low density lipoprotein receptor-related . . .".

Mao et al., Gene, vol. 302 (2003), pp. 179-183, Kremen2 modulates Dickkopf2 activity during Wnt/LRP6 signaling.

Mao et al., Molecular Cell, vol. 7 (2001), pp. 801-809, "Low-density lipoprotein receptor-related protein-5 binds to axin and regulates the canonical Wnt signaling pathway".

Mao et al., Nature, vol. 411 (2001), pp. 321-325, "LDL-receptor-related protein 6 is a receptor for Dickkopf proteins".

Mao et al., Nature, vol. 410 (2002), pp. 664-667, "Kremen proteins are Dickkopf receptors that regulate Wnt/beta-protein signaling".

Patel et al., N. Eng. J. Med., vol. 346 (2002), pp. 1572-1574, "Regulation of bone formation and vision by LRP5".

Semenov et al., Current Biology, vol. 11 (2001), pp. 951-961, "Head inducer Dickkopf-1 is a ligand for Wnt coreceptor LRP6".

Sjolander et al., Anal. Chem., vol. 63 (1991), pp. 2338-2345, "Integrated fluid handlding system for biomolecular interaction analysis".

Szabo et al., Current Opin. in Structural Biol., vol. 5 (1995), pp. 699-705, "Surface plasmon resonance and its use in biomolecular interaction analysis (BIA)".

Yuan et al., J. of Biol. Chem., vol. 274 (1999), pp. 30419-30423, "Suppression of glycogen synthase kinase activity is not sufficient for leukemia enhancer factor-1 activation".

Yamaguchi et al., Biochem. and Biophys. Res. Commun., vol. 220 (1996), pp. 366-371, "Effects of BMP-2, BMP-4, and BMP-6 on osteoblastic differentiation of bone marrow-derived stromal cell lines, ST2 and . . . ".

* cited by examiner

Nucleotide Sequence of Rhesus Monkey Dkk-1 (SEQ ID NO:1)

```
atgatggctc tgggcgcagc aggagctgcc cgggtcttgg tcgcgctggt agcggcggct   60
cttggcggcc accctctgct gggagtgagc gccaccttga actcggttct caattccaac  120
gcgatcaaga acctgccccc accgctgggc ggcgctgcgg ggcacccagg ctctgcagtc  180
agcgccgcgc caggaattct gtacccgggc gggaataagt accagaccat tgacaactac  240
cagccgtacc cgtgcgcaga ggatgaggag tgcggcactg atgagtactg cgctagtccc  300
acccgcggag gggacgcggg cgtgcaaatc tgtctcgcct gcaggaagcg ccgaaaacgc  360
tgcatgcgtc acgctatgtg ctgccccggg aattactgca aaatggaat atgtgtgtct  420
tctgatcaaa ataatttccg aggggaaatt gaggaaacca ttactgaaag ctttggtaat  480
gatcatagca ctttggatgg gtattccaga agaacaacat tgtcttcaaa aatgtatcac  540
agcaaaggac aagaaggttc tgtgtgtctc cggtcatcag actgtgccac aggactgtgt  600
tgtgctagac acttctggtc caagatctgt aaacctgtcc tcaaagaagg tcaagtgtgt  660
accaagcata gaagaaaagg ctctcatggg ctagaaatat ccagcgttg ttactgcgga  720
gaaggtctgt cttgccggat acagaaagat caccatcaag ccagtaattc ttctaggctt  780
cacacttgtc agagacacta a                                            801
```

FIG. 1

Amino Acid Sequence of Dkk-1 Protein (SEQ ID NO:2)

```
  1 MMALGAAGAA RVLVALVAAA LGGHPLLGVS ATLNSVLNSN AIKNLPPPLG GAAGHPGSAV
 61 SAAPGILYPG GNKYQTIDNY QPYPCAEDEE CGTDEYCASP TRGGDAGVQI CLACRKRRKR
121 CMRHAMCCPG NYCKNGICVS SDQNNFRGEI EETITESFGN DHSTLDGYSR RTTLSSKMYH
181 SKGQEGSVCL RSSDCATGLC CARHFWSKIC KPVLKEGQVC TKHRRKGSHG LEIFQRCYCG
241 EGLSCRIQKD HHQASNSSRL HTCQRH
```

FIG.2

Alignment of Dickkopf-1 Nucleotide Sequences

```
                        101                                                            150
Rhesus_Dickkopf-1 .......... .......... .......... ..........A TGATGGCTCT
   Human_Dickkopf1 .......... .......... .......... ..........A TGATGGCTCT 151                                                            200
Rhesus_Dickkopf-1 GGGCGCAGCA GGAGCTGCCC GGGTCTTGGT CGCGCTGGTA GCGGCGGCTC
   Human_Dickkopf1 GGGCGCAGCG GGAGCTACCC GGGTCTTTGT CGCGATGGTA GCGGCGGCTC 201                                                            250
Rhesus_Dickkopf-1 TTGGCGGCCA CCCTCTGCTG GGAGTGAGCG CCACCTTGAA CTCGGTTCTC
   Human_Dickkopf1 TCGGCGGCCA CCCTCTGCTG GGAGTGAGCG CCACCTTGAA CTCGGTTCTC 251                                                            300
Rhesus_Dickkopf-1 AATTCCAACG CGATCAAGAA CCTGCCCCCA CCGCTGGGCG GCGCTGCGGG
   Human_Dickkopf1 AATTCCAACG CTATCAAGAA CCTGCCCCCA CCGCTGGGCG GCGCTGCGGG 301                                                            350
Rhesus_Dickkopf-1 GCACCCAGGC TCTGCAGTCA GCGCCGCGCC AGGAATTCTG TACCCGGGCG
   Human_Dickkopf1 GCACCCAGGC TCTGCAGTCA GCGCCGCGCC GGGAATCCTG TACCCGGGCG 351                                                            400
Rhesus_Dickkopf-1 GGAATAAGTA CCAGACCATT GACAACTACC AGCCGTACCC GTGCGCAGAG
   Human_Dickkopf1 GGAATAAGTA CCAGACCATT GACAACTACC AGCCGTACCC GTGCGCAGAG 401                                                            450
Rhesus_Dickkopf-1 GATGAGGAGT GCGGCACTGA TGAGTACTGC GCTAGTCCCA CCCGCGGAGG
   Human_Dickkopf1 GACGAGGAGT GCGGCACTGA TGAGTACTGC GCTAGTCCCA CCCGCGGAGG 451                                                            500
Rhesus_Dickkopf-1 GGACGCGGGC GTGCAAATCT GTCTCGCCTG CAGGAAGCGC CGAAAACGCT
   Human_Dickkopf1 GGACGCGGGC GTGCAAATCT GTCTCGCCTG CAGGAAGCGC CGAAAACGCT 501                                                            550
Rhesus_Dickkopf-1 GCATGCGTCA CGCTATGTGC TGCCCCGGGA ATTACTGCAA AAATGGAATA
   Human_Dickkopf1 GCATGCGTCA CGCTATGTGC TGCCCCGGGA ATTACTGCAA AAATGGAATA
```

FIG.3A

```
                     551                                                      600
Rhesus_Dickkopf-1  TGTGTGTCTT CTGATCAAAA TAATTTCCGA GGGGAAATTG AGGAAACCAT
  Human_Dickkopf1  TGTGTGTCTT CTGATCAAAA TCATTTCCGA GGAGAAATTG AGGAAACCAT 601                                                      650
Rhesus_Dickkopf-1  TACTGAAAGC TTTGGTAATG ATCATAGCAC TTTGGATGGG TATTCCAGAA
  Human_Dickkopf1  CACTGAAAGC TTTGGTAATG ATCATAGCAC CTTGGATGGG TATTCCAGAA 651                                                      700
Rhesus_Dickkopf-1  GAACAACATT GTCTTCAAAA ATGTATCACA GCAAAGGACA AGAAGGTTCT
  Human_Dickkopf1  GAACCACCTT GTCTTCAAAA ATGTATCACA CCAAAGGACA AGAAGGTTCT 701                                                      750
Rhesus_Dickkopf-1  GTGTGTCTCC GGTCATCAGA CTGTGCCACA GGACTGTGTT GTGCTAGACA
  Human_Dickkopf1  GTTTGTCTCC GGTCATCAGA CTGTGCCTCA GGATTGTGTT GTGCTAGACA 751                                                      800
Rhesus_Dickkopf-1  CTTCTGGTCC AAGATCTGTA AACCTGTCCT CAAAGAAGGT CAAGTGTGTA
  Human_Dickkopf1  CTTCTGGTCC AAGATCTGTA AACCTGTCCT GAAAGAAGGT CAAGTGTGTA 801                                                      850
Rhesus_Dickkopf-1  CCAAGCATAG AAGAAAAGGC TCTCATGGGC TAGAAATATT CCAGCGTTGT
  Human_Dickkopf1  CCAAGCATAG GAGAAAAGGC TCTCATGGAC TAGAAATATT CCAGCGTTGT 851                                                      900
Rhesus_Dickkopf-1  TACTGCGGAG AAGGTCTGTC TTGCCGGATA CAGAAAGATC ACCATCAAGC
  Human_Dickkopf1  TACTGTGGAG AAGGTCTGTC TTGCCGGATA CAGAAAGATC ACCATCAAGC 901                                950
Rhesus_Dickkopf-1  CAGTAATTCT TCTAGGCTTC ACACTTGTCA GAGACACTAA (SEQ ID NO:1)
  Human_Dickkopf1  CAGTAATTCT TCTAGGCTTC ACACTTGTCA GAGACACTAA (SEQ ID NO:20)
```

FIG.3B

Alignment of Dickkopf-1 Amino Acid Sequences

```
              1                                                        50
Human_Dkk1    MMALGAAGAT RVFVAMVAAA LGGHPLLGVS ATLNSVLN.S NAIKNLPPPL
Mouse_Dkk1    MMVVCAPAAV RFLAVFTMMA LCSLPLLGAS ATLNSVLINS NAIKNLPPPL
Rhesus_Dkk1   MMALGAAGAA RVLVALVAAA LGGHPLLGVS ATLNSVLN.S NAIKNLPPPL 51                                                       100
Human_Dkk1    GGAAGHPGSA VSAAPGILYP GGNKYQTIDN YQPYPCAEDE ECGTDEYCAS
Mouse_Dkk1    GGAGGQPGSA VSVAPGVLYE GGNKYQTLDN YQPYPCAEDE ECGSDEYCSS
Rhesus_Dkk1   GGAAGHPGSA VSAAPGILYP GGNKYQTIDN YQPYPCAEDE ECGTDEYCAS 101                                                      150
Human Dkk1    PTR..GGDAG VQICLACRKR RKRCMRHAMC CPGNYCKNGI CVSSDQNHF.
Mouse_Dkk1    PSRGAAGVGG VQICLACRKR RKRCMTHAMC CPGNYCKNGI CMPSDHSHFP
Rhesus_Dkk1   PTR..GGDAG VQICLACRKR RKRCMRHAMC CPGNYCKNGI CVSSDQNNF.

151                                                      200
Human_Dkk1    RGEIEETITE SFGNDH..ST LDGYSRRTTL SSKMYHTKGQ EGSVCLRSSD
Mouse_Dkk1    RGEIEESIIE NLGNDHNAAA GDGYPRRTTL TSKIYHTKGQ EGSVCLRSSD
Rhesus_Dkk1   RGEIEETITE SFGNDH..ST LDGYSRRTTL SSKMYHSKGQ EGSVCLRSSD 201                                                      250
Human_Dkk1    CASGLCCARH FWSKICKPVL KEGQVCTKHR RKGSHGLEIF QRCYCGEGLS
Mouse_Dkk1    CAAGLCCARH FWSKICKPVL KEGQVCTKHK RKGSHGLEIF QRCYCGEGLA
Rhesus_Dkk1   CATGLCCARH FWSKICKPVL KEGQVCTKHR RKGSHGLEIF QRCYCGEGLS 251           272
Human_Dkk1    CRIQKDHHQA SNSSRLHTCQ RH (SEQ ID NO:21)
Mouse_Dkk1    CRIQKDHHQA SNSSRLHTCQ RH (SEQ ID NO:22)
Rhesus_Dkk1   CRIQKDHHQA SNSSRLHTCQ RH (SEQ ID NO:2)
```

FIG.4 ated with high bone mass trait (HBM), an autosomal domi

RHESUS MONKEY DICKKOPF-1, NUCLEOTIDES ENCODING SAME, AND USES THEREOF

CROSS REFERENCE TO RELATED APPLICATIONS

This patent application claims benefit of International Patent Application No. PCT/US2004/038489, which was filed 12 Nov. 2004, and U.S. Provisional application No. 60/520,708, which was filed 17 Nov. 2003.

FIELD OF THE INVENTION

The present invention relates generally to the therapy of osteoporosis and other conditions characterized by bone loss or insufficient bone mass. More specifically, the present invention relates to rhesus monkey dickkopf-1, herein designated rhDkk-1, to isolated nucleic acid molecules that encode this protein, and to recombinant vectors and hosts comprising DNA encoding this protein. This invention also relates to methods for identifying compounds that interfere with the interaction between rhDkk-1 and its receptors, said compounds being useful for stimulating bone formation for the treatment of osteoporosis and other bone loss disorders.

BACKGROUND OF THE INVENTION

The skeletal disorder osteoporosis is the leading cause of morbidity in the elderly. Osteoporosis is characterized by bone loss resulting from an imbalance between bone resorption (destruction) and bone formation. This condition leads to an increased risk of bone fractures, which may occur following low levels of trauma. In the United States, there are currently about 20 million people with detectable fractures of the vertebrae due to osteoporosis. Mortality due to bone fractures is not uncommon among the elderly patient population Elderly, post-menopausal women are at the highest risk of developing osteoporosis due to a deficiency of estrogen, which is necessary for proper bone maintenance. Insufficient estrogen levels lead to increased production and longevity of destructive osteoclasts, which, in turn, leads to increased bone resorption. As a result, an average of 5% bone loss is observed in the vertebrae per year. Although less common, osteoporosis also affects elderly men. The existence of osteoporosis in elderly men may also be due, in part, to insufficient estrogen levels caused by a decrease in circulating testosterone.

Therapeutic strategies for overcoming bone loss include both the prevention of bone resorption and the stimulation of bone growth. The majority of therapeutic targets that have led to efficacious osteoporosis treatments fall into the former category. Thus, the first line of treatment/prevention of this condition has historically been the inhibition of bone resorption using compounds such as bisphosphonates, estrogens, selective estrogen receptor modulators (SERMs) and calcitonin. Because inhibition of bone resorption cannot restore bone mass, this approach is an ineffective treatment for patients who have already lost a significant amount of bone. Additionally, the effectiveness of osteoporosis treatments that function by this mechanism is not consistent across the skeletal anatomy because the rate of bone turnover differs from one site to another. For example, the bone turnover rate is higher in the trabecular bone of the vertebrae than in the cortex of the long bones; thus, bone resorption inhibitors are less effective in increasing hip bone mineral density (BMD) and preventing hip fracture. Therefore, osteoanabolic agents, which increase cortical/periosteal bone formation and bone mass at long bones, would address an unmet need in the treatment of osteoporosis, especially for patients with high risk of hip fractures.

One potential therapeutic target for metabolic disorders, including osteoporosis, is the low-density lipoprotein receptor related protein 5 (LRP5). LRP5 belongs to the low density lipoprotein receptor (LDLR) gene family of cell surface receptors, characterized by cysteine-rich, complement-type LDLR ligand binding domains. LRP5 was isolated based on its proximity to the locus of osteoporosis pseudoglioma syndrome (OPG), an autosomal recessive disorder characterized by severe osteoporosis (Hey, et al. *Gene* 216: 103-111 (1998); Todd et al., WO 98/46743). Additional support for the notion that LRP5 represents a therapeutic target for osteoporosis comes from the observation that loss of function mutations of LRP5 lead to OPG (Gong et al, *Cell* 107: 513-523 (2001)).

Interestingly, aberrant expression of LRP5 is also associated with high bone mass trait (HBM), an autosomal dominant human genetic skeletal condition characterized by strikingly increased bone mass. Positional cloning of the HBM mutation demonstrated that HBM results from a G171V mutation of the LRP5 gene which leads to a gain of function (Little et al, *Am. J. Hum. Genet.* 70: 11-19 (2002)). These findings, together with the fact that null mutation of LRP5 in mice results in severe bone loss (Kato, *J. Cell Biol.* 157(2): 303-314 (2002)), demonstrated an essential role for LRP5 in bone formation and bone mass in humans.

Despite its specific role in stimulating bone growth, the LRP5 gene was shown to have a nearly ubiquitous expression profile. The mechanism by which activation of LRP5 leads to osteogenesis is not known. At the molecular level, it was recently shown that LRP5 and a closely related LRP6 are involved in Wnt signaling as co-receptors for Wnt. Wnt genes encode secreted proteins implicated in a diverse array of developmental and adult physiological processes, such as mediating cell growth and differentiation in the central nervous system. It was also shown that LRP5 and LRP6 are receptors for the secreted protein dickkopf-1 (Dkk-1) and that their association with Dkk-1 represses Wnt signaling (Mao et al., *Nature* 411: 321-325 (2001); Semenov et al, *Curr. Biol.*, (2001); Bafico et al, *Nat Cell Biol* 3: 683-686 (2001)).

Dickkopf-1 is a secreted protein that participates in embryonic head induction and antagonizes Wnt (Glinka et al., *Nature* 391: 357-362 (1998)). The amino acid sequence of human Dkk-1 and nucleotides encoding it have been described (McCarthy, WO 00/52047; and Krupnick et al., *Gene* 238: 301-313(1999)). Expression of Dkk-1 in human was thought to be restricted to placenta, suggesting a role for Dkk-1 in embryonic development (Krupnick et al., supra). Allen and colleagues (WO 02/092015) describe assays relating to the interaction between LRP5, HBM or LRP6 with Dkk-1.

Human Dkk-1 is a member of a Dickkopf gene family which includes Dkk-1, Dkk-2, Dkk-3, and Dkk-4 (Krupnick et al., supra). Although Dkk-1 and Dkk-4 have been shown to suppress Wnt-induced secondary axis induction in *Xenopus* embryos, neither block axis induction triggered by *Xenopus* Dishevelled or Frizzled, suggesting that their Wnt inhibitory activity is upstream of Frizzled in the Wnt signaling pathway (Krupnick et al., supra). It has been suggested that Dkk-1 or Dkk-2 might have an inhibitory effect on bone formation, making them potential targets for the prevention or treatment of osteoporosis (Patel and Karensky, *N. Eng. J. Med.* 346: 1572-1573 (2002); Boyden et al., *N. Eng. J. Med.* 346: 1513-1521 (2002)).

In addition to LRP5 and LRP6, recent studies indicate that the transmembrane proteins kremen1 and kremen2 are Dkk-1 receptors. The interaction between the kremen receptors and Dkk-1 blocks Wnt signaling, thereby regulating central nervous system patterning during embryonic development (Mao et al., *Nature* 417: 664-667 (2002); Davidson et al., *Development* 129: 5587-96 (2002)). Evidence suggests that Dkk-1 inhibits LRP5 or LRP6-activated Wnt signaling by cooperating with kremen to form a ternary complex with LRP5 or LRP6. The ternary complex is rapidly endocytosed, which removes the LPR5 or LRP6 from the membrane, thus preventing LPR5 or LPR6 from binding Wnt.

Despite the existence of osteoporosis therapies which work by preventing bone loss, it would be advantageous to identify molecules that act selectively in bone tissue to activate Wnt signaling, thus stimulating bone formation. Such compounds would be an ideal treatment for osteoporosis as a monotherapy or in combination with inhibitors of bone resorption, such as bisphosphonates, estrogens, SERMs, cathepsin K inhibitors, $\alpha V\beta 3$ antagonists, calcitonin, proton pump inhibitors.

SUMMARY OF THE INVENTION

The present invention provides methods for identifying analytes which interfere with the interaction between the *Macaca mulatta* (rhesus monkey) Dickkopf-1 (rhDkk-1) protein and a homologous or heterologous Dkk receptor or binding partner. In one aspect, the present invention provides an isolated rhDkk-1 protein, isolated nucleic acid molecules which encode the rhDkk-1 protein, and recombinant vectors and hosts comprising the nucleic acid encoding the rhDkk-1 protein. In another aspect, the present invention provides methods for using the isolated rhDkk-1 protein to identify analytes which interfere with the interaction between the rhDkk-1 protein and one or more homologous or heterologous Dkk receptors or binding partners such as human LRP5, LRP6, kremen1, or kremen2 and which stimulate bone formation. Analytes identified using one or more of the methods disclosed herein are useful for treating osteoporosis and other bone mass disorders characterized by bone loss.

Therefore, the present invention provides an isolated nucleic acid molecule comprising a nucleotide sequence encoding a rhDkk-1 protein which has an amino acid sequence as set forth in SEQ ID NO:2. In further embodiments, the isolated nucleic acid is a DNA molecule, an RNA molecule, or a cDNA molecule. In a further still embodiment, the nucleic acid has a nucleotide sequence substantially as set forth in SEQ ID NO:1. The present invention further provides a protein comprising an amino acid sequence as set forth in SEQ ID NO:2. It is preferable that the rhDkk-1 protein be capable of binding a Dkk receptor, preferably, a Dkk receptor selected from the group consisting of low-density lipoprotein receptor protein 5 (LRP5), low-density lipoprotein receptor protein 6 (LRP6), kremen1, and kremen2. It is particularly preferable that the rhDkk-1 be capable of binding LRP5 or LRP6.

A preferred aspect of the present invention is a substantially purified form of a rhesus monkey Dkk-1 protein which comprises the amino acid sequence disclosed in FIG. 2 (SEQ ID NO:2).

Another preferred aspect of the present invention is a substantially purified, fully processed (including proteolytic processing, glycosylation and/or phosphorylation), mature rhDkk-1 protein obtained from a recombinant host cell containing a DNA expression vector comprising a sequence of nucleotides as set forth in SEQ ID NO:1, which express the rhDkk-1 protein. It is especially preferred that the recombinant host cell be a eukaryotic host cell, such as a mammalian cell line.

The present invention further provides an antibody which binds a protein comprising an amino acid sequence as set forth in SEQ ID NO:2. In particular embodiments, the antibody is selected from the group consisting of polyclonal antibodies, monoclonal antibodies, single VH chain antibodies, Fab fragments, and recombinant antibodies. In embodiments in which the antibody is a recombinant antibody, the recombinant antibody includes recombinant antibodies selected from the group consisting of scFv polypeptides and VH chain polypeptides.

The present invention further provides a vector comprising a nucleic acid encoding a rhDkk-1 protein which has an amino acid sequence as set forth in SEQ ID NO:2. In particular embodiments, the vector is selected from the group consisting of plasmids and viruses. In further still embodiments, the nucleic acid is operably linked to a promoter which includes one or more regulatory sequences which enable expression of the polypeptide. In particular embodiments, the promoter provides inducible expression and in other embodiments, the promoter provides constitutive expression. In a further still embodiment, the nucleic acid includes the nucleotide sequence set forth in SEQ ID NO:1.

The present invention further provides a cell comprising a nucleic acid encoding a rhDkk-1 protein which has an amino acid sequence as set forth in SEQ ID NO:2 wherein the nucleic acid is operably linked to a heterologous promoter. The cell can be a prokaryote cell or a eukaryote cell. In embodiments which include eukaryote cells, the cell can be of mammalian, insect, amphibian, fungal, or plant origin.

The present invention further provides a method for producing a rhDkk-1 protein which binds a homologous or heterologous low-density lipoprotein receptor protein 5 (LRP5) comprising (a) providing a nucleic acid encoding the rhDkk-1 protein operably linked to a heterologous promoter; (b) introducing the nucleic acid into a cell to produce a recombinant cell; and (c) culturing the recombinant cell under conditions which allows expression of the rhDkk-1 protein to produce the rhDkk-1. In further embodiments, the nucleic acid encodes a protein which comprises an amino acid sequence as set forth in SEQ ID NO:2 or the nucleic acid has a nucleotide sequence as set forth in SEQ ID NO:1. In some embodiments, the cell is a prokaryote cell and in other embodiments, the cell is a eukaryote cell. In further embodiments, the LRP5 is a human LRP5.

The present invention also provides methods for identifying analytes that disrupt the molecular and/or functional interaction between Dkk-1 and at least one Dkk-1 receptor. In preferred embodiments, the DKK-1 receptor is selected from the group consisting of: LRP5, LRP6, kremen1 and kremen2 and combinations thereof. One of skill in the art will recognize that a number of molecular techniques may be employed to identify such analytes; including, but not limited to: (i) cell-based binding assays, (ii) cell-free binding assays, (iii) osteoblast differentiation assays in preosteoblastic cells and (iv) cell based reporter assays.

Such analytes, identified with the methods listed above, act in bone tissue to modulate Wnt signaling to stimulate bone formation. Such analytes are ideal for treatment of osteoporosis in women and men as a monotherapy or in combination with inhibitors of bone resorption, such as bisphosphonates, estrogens, SERMs, cathepsin K inhibitors, $\alpha V\beta 3$ antagonists, calcitonin, proton pump inhibitors.

For use in the screening methods described herein, the Dkk-1 receptor is selected from the group consisting of low-density lipoprotein receptor protein 5 (LRP5), low-density lipoprotein receptor protein 6 (LRP6), kremen1, kremen2, and combinations thereof. In alternative embodiments, a first Dkk-1 receptor and a second Dkk-1 receptor are used; wherein the first Dkk-1 receptor is selected from the group consisting of: LRP5 and LRP6 and the second Dkk-1 receptor is selected from the group consisting of: kremen1 and kremen2. In further embodiments, the Dkk-1 receptor is heterologous and in further still embodiments, the Dkk-1 receptor is of human origin. In particularly preferred embodiments of the methods described herein, the Dkk-1 receptors are LRP5 and kremen2. In further embodiments, the Dkk-1 receptor comprises a combination of LRP5 and LRP6 together with Kremen1 and Kremen2.

The present invention further provides a method for determining whether an analyte is an antagonist of Dickkopf 1 (Dkk-1) comprising providing a polypeptide comprising the extracellular domain of a Dkk-1 receptor; contacting the polypeptide with a rhesus monkey Dkk-1 (rhDkk-1) and the analyte; and determining whether binding of the rhDkk-1 to the polypeptide is decreased in the presence of the analyte, wherein a decrease in the binding indicates that the analyte is an rhDkk-1 antagonist.

In a further aspect of the above method, the Dkk-1 receptor is low-density lipoprotein receptor related protein 5 (LRP5) or low density lipoprotein receptor related protein 6 (LRP6) or the receptor is kremen1 or kremen2.

In further still aspects, the rhDkk-1 is labeled with a detectable molecule, for example, alkaline phosphatase, radioactive isotope, lanthanide such as europium, or a fluorescent dye, or the rhDkk-1 is a fusion protein in which the amino or carboxyl terminus of the rhDkk-1 is covalently linked to a detectable protein or polypeptide, including but not limited to, c-myc, which can be detected using an antibody against the c-myc, or an enzyme, for example, alkaline phosphatase, which can be detected in a colorimetric assay, or other detectable protein, for example, luciferase or Green fluorescent protein, which can detected by monitoring emission of light or fluorescence.

The present invention further provides a method for determining whether an analyte is an antagonist of Dickkopf-4 (Dkk-1) protein, which comprises providing a recombinant cell which produces one or more Dkk-1 receptors; introducing a reporter expression vector into the recombinant cell which comprises a reporter gene operably linked to a promoter responsive to Wnt-mediated signal transduction to provide a second recombinant cell; exposing the second recombinant cell to the analyte and to a rhesus monkey Dkk-1 (rhDkk-1); and measuring expression of the reporter gene, wherein an increase in expression of the reporter gene in the presence of the analyte relative to expression of the reporter gene in the absence of the analyte indicates that the analyte is a Dkk-1 antagonist.

In further aspects of the above method, the one or more Dkk-1 receptors are selected from the group consisting of low-density lipoprotein receptor protein 5 (LRP5), low-density lipoprotein receptor protein 6 (LRP6), kremen1, kremen2, and combinations thereof.

In particular aspects, the reporter gene is selected from the group consisting of the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites. In further still aspects of the above method, the promoter comprises one or more lymphoid enhancer factor/T cell factor (TCF/LEF) binding sites.

In further still aspects of the above method, the rhDkk-1 is provided exogenously as an isolated rhDkk-1 protein or as a component of a medium obtained from a culture comprising a second recombinant cell which expresses the rhDkk-1 or the rhDkk-1 is provided by cotransfecting the second recombinant cell with an expression vector encoding the rhDkk-1.

In further still aspects of the above method, a Wnt ligand is provided exogenously to the second recombinant cell as an isolated Wnt ligand or as a component of a medium obtained from a culture comprising a second recombinant cell which expresses the Wnt ligand or the Wnt ligand is provided to the second recombinant cell by cotransfecting the second recombinant cell with an expression vector encoding the Wnt ligand.

The present invention further provides a method for determining whether an analyte interferes with binding of Dickkopf-4 (Dkk-1) protein to a Dkk-1 receptor, which comprises providing a recombinant cell which expresses the Dkk-1 receptor, culturing the recombinant cell in a culture medium which contains a rhesus monkey Dkk-1 (rhDkk-1) protein and the analyte; and measuring the rhDkk-1 bound to the rhDkk-1 receptor, wherein a decrease in the rhDkk-1 protein bound to the Dkk-1 receptor in the presence of the analyte relative to rhDkk-1 protein bound in the absence of the analyte indicates that the analyte interferes with the binding of the Dkk-1 protein to the Dkk-1 receptor.

In further aspects of the above method, the Dkk-1 receptor is selected from the group consisting of low-density lipoprotein receptor protein 5 (LRP5), low-density lipoprotein receptor protein 6 (LRP6), kremen1, kremen2, and combinations thereof.

In further still aspects, the rhDkk-1 is labeled with a detectable molecule, for example, alkaline phosphatase, radioactive isotope, lanthanide such as europium, or a fluorescent dye, or the rhDkk-1 is a fusion protein in which the amino or carboxyl terminus of the rhDkk-1 is covalently linked to a detectable protein or polypeptide, including but not limited to, c-myc, which can be detected using an antibody against the c-myc, or an enzyme, for example, alkaline phosphatase, which can be detected in a colorimetric assay, or other detectable protein, for example, luciferase or Green fluorescent protein, which can detected by monitoring emission of light or fluorescence.

The present invention further provides a method of identifying an analyte that induces Wnt signaling comprising: transfecting a recombinant cell expressing one or more Dkk-1 receptors with a reporter gene operably linked to a promoter responsive to Wnt-mediated signal transduction; exposing the cells to an analyte, rhesus monkey Dkk-1 (rhDkk-1), and a Wnt ligand; measuring expression of the reporter gene, wherein an increase in expression of the reporter gene in the presence of the analyte relative to expression of the reporter gene in the absence of the analyte indicates that the analyte induces the Wnt signaling.

In further aspects of the above methods, the one or more Dkk-1 receptors are selected from the group consisting of low-density lipoprotein receptor protein 5 (LRP5), low-density lipoprotein receptor protein 6 (LRP6), kremen1, kremen2, and combinations thereof.

In particular aspects, the reporter gene is selected from the group consisting of the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites. In further still aspects of the above method, the promoter comprises one or more lymphoid enhancer factor/T cell factor (TCF/LEF) binding sites.

In further still aspects of the above method, the rhDkk-1 is provided exogenously as an isolated rhDkk-1 protein or as a component of a medium obtained from a culture comprising a second recombinant cell which expresses the rhDkk-1 or the rhDkk-1 is provided by cotransfecting the second recombinant cell with an expression vector encoding the rhDkk-1.

In further still aspects of the above method, a Wnt ligand is provided exogenously to the second recombinant cell as an isolated Wnt ligand or as a component of a medium obtained from a culture comprising a second recombinant cell which expresses the Wnt ligand or the Wnt ligand is provided to the second recombinant cell by cotransfecting the second recombinant cell with an expression vector encoding the Wnt ligand.

The present invention further provides a method for determining whether a compound inhibits Dickkopf 1 (Dkk-1) protein suppression of osteoblast differentiation comprising providing pluripotent cells which can be induced to differentiate along an osteoblast lineage; transfecting the cells with a first expression vector which expresses a rhesus monkey Dkk-1 (rhDkk-1) protein, a second expression vector, which expresses low-density lipoprotein receptor protein (LRP), and a third expression vector which expresses Wnt protein; incubating the cells in a medium containing the analyte for a time sufficient for expression of the rhDkk-1 protein, LRP, and Wnt protein; and measuring expression of one or more osteoblastic markers wherein expression of the one or more markers indicates that the analyte inhibits rhDkk-1 suppression of osteoblast differentiation.

In further aspects of the above methods, the pluripotent cell is a pluripotent marrow stromal cell or a pluripotent mesenchymal cell. In a further still embodiment, the pluripotent cell is selected from the group consisting of ST2 cells and C3H10T1/2 cells. In further still embodiments, the LRP is selected from the group consisting of LRP5 or LRP6. In a further still embodiment, the one or more osteoblastic markers are selected from the group consisting of alkaline phosphatase, Bglap, and Runx2. Preferably, the osteoblastic marker is alkaline phosphatase activity. In further embodiments, the LRP5 and Wnt protein are heterologous and in further still embodiments, the LRP5 and Wnt protein are of human origin.

As used throughout the specification and in the appended claims, the singular forms "a," "an," and "the" include the plural reference unless the context clearly dictates otherwise.

As used throughout the specification and appended claims, the following definitions and abbreviations apply.

The term "rhDkk-1 protein" means that the rhDkk-1 protein is of rhesus monkey origin, either isolated from rhesus monkey tissue, produced from a nucleic acid obtained from the rhesus monkey by recombinant means, produced from a nucleic acid synthesized in vitro but which encodes the rhDkk-1 protein, or synthesized in vitro. The term further includes biologically active fragments or portions of the rhDkk-1 protein.

The term "Dkk-1 protein" means that the Dkk-1 protein is not of rhesus monkey origin. The Dkk-1 protein can be from another organism, for example, insects such as *Drosophila*, amphibians such as *Xenopus*, mammals such as rat and mouse, and humans. The Dkk-1 protein can either be isolated from tissue of the organism, produced from a nucleic acid obtained from the organism by recombinant means, produced from a nucleic acid synthesized in vitro but which encodes the Dkk-1 protein, or synthesized in vitro. The term further includes biologically active fragments or portions of the Dkk-1 protein.

The term "Dkk protein" means that the protein is selected from the group consisting of Dkk-1 protein, Dkk-2 protein, Dkk-3 protein, and Dkk-1 protein. The Dkk protein can be of rhesus monkey origin or originate from another organism, for example, insects such as *Drosophila*, amphibians such as *Xenopus*, mammals such as rat and mouse, and humans. The Dkk protein can either be isolated from tissue of the rhesus monkey or organism or produced from a nucleic acid obtained from the rhesus monkey or organism by recombinant means, produced from a nucleic acid synthesized in vitro but which encodes the Dkk protein, or synthesized in vitro. The term further includes biologically active fragments or portions of the Dkk protein.

The term "Dkk receptor" means a binding partner of Dkk-1 which binds or interacts with the rhDkk-1 protein or Dkk-1 protein. The term further includes binding partners which can bind one or more Dkk proteins selected from the group consisting of Dkk-1 protein, Dkk-2 protein, Dkk-3 protein, and Dkk-4 protein regardless of whether they originate from the rhesus monkey, another organism, expressed from a nucleic acid synthesized in vitro, or synthesized in vitro. Examples of binding partners include LRP5, LRP6, kremen1, and kremen2. The term further includes biologically active fragments or portions of the binding partner.

The term "homologous Dkk receptor" means a Dkk receptor of rhesus monkey origin. In other words, the Dkk receptor is isolated from the rhesus monkey or obtained from recombinant cells expressing the receptor from DNA encoding the rhesus monkey receptor. The homologous Dkk receptor can be a receptor specific for rhDkk-1 protein or Dkk-1 protein or a receptor which can bind one or more of Dkk-1 protein, Dkk-2 protein, Dkk-3 protein, or Dkk-1 protein.

The term "heterologous Dkk receptor" means a Dkk receptor not of rhesus monkey origin. For example, the Dkk receptor is isolated from a human or obtained from recombinant cells expressing the receptor from DNA encoding the human receptor. The heterologous Dkk receptor can be a receptor specific for rhDkk-1 protein or Dkk-1 protein or a receptor which can bind one or more of Dkk-1 protein, Dkk-2 protein, Dkk-3 protein, or Dkk-1 protein.

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to a nucleotide or gene sequence that is to be expressed from a vector, for example, the nucleotide or gene sequence encoding rhDkk-1. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The term "vector" refers to some means by which DNA fragments can be introduced into a host organism or host tissue. There are various types of vectors including plasmids, viruses (including adenovirus), bacteriophages and cosmids.

"Substantially free from other nucleic acids" means at least 90%, preferably 95%, more preferably 99%, and even more preferably 99.9%, free of other nucleic acids. As used interchangeably, the terms "substantially free from other nucleic acids," "substantially purified," "isolated nucleic acid" or "purified nucleic acid" also refer to DNA molecules which comprise a coding region for a rhesus Dkk-1 protein that has been purified away from other cellular components. Thus, a rhesus Dkk-1 DNA preparation that is substantially free from other nucleic acids will contain, as a percent of its total nucleic acid, no more than 10%, preferably no more than 5%, more preferably no more than 1%, and even more preferably no more than 0.1%, of non-rhesus Dkk-1 nucleic acids. Whether a given rhesus Dkk-1 DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

"Substantially free from other proteins" or "substantially purified" means at least 90%, preferably 95%, more preferably 99%, and even more preferably 99.9%, free of other proteins. Thus, a rhesus monkey Dkk-1 protein preparation that is substantially free from other proteins will contain, as a percent of its total protein, no more than 10%, preferably no more than 5%, more preferably no more than 1%, and even more preferably no more than 0.1%, of non-rhesus monkey Dkk-1 proteins. Whether a given rhesus monkey Dkk-1 protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

As used interchangeably, the terms "substantially free from other proteins" or "substantially purified," or "isolated rhesus monkey Dkk-1 protein" or "purified rhesus monkey Dkk-1 protein" also refer to rhesus monkey Dkk-1 protein that has been isolated from a natural source. Use of the term "isolated" or "purified" indicates that rhesus monkey Dkk-1 protein has been removed from its normal cellular environment. Thus, an isolated rhesus monkey Dkk-1 protein may be in a cell-free solution or placed in a different cellular environment from that in which it occurs naturally. The term isolated does not imply that an isolated rhesus monkey Dkk-1 protein is the only protein present, but instead means that an isolated rhDkk-1 protein is substantially free of other proteins and non-amino acid material (e.g., nucleic acids, lipids, carbohydrates) naturally associated with the rhDkk-1 protein in vivo. Thus, a rhesus monkey Dkk-1 protein that is recombinantly expressed in a prokaryotic or eukaryotic cell and substantially purified from this host cell which does not naturally (i.e., without intervention) express this rhDkk-1 protein is of course "isolated rhesus monkey Dkk-1 protein" under any circumstances referred to herein.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

The abbreviation "ORF" refers to the open reading frame of a gene.

The term "treatment" refers to both therapeutic treatment and prophylactic or preventative measures. Those in need of treatment include those already with the disorder as well as those prone to have the disorder or those in which the disorder is to be prevented.

A "disorder" is any condition that would benefit from treatment with molecules identified by the methods described herein. This includes chronic and acute disorders or diseases including those pathological conditions which predispose the mammal to the disorder in question. The methods of the present invention are intended to identify molecules to be used for the treatment of disorders or conditions associated with aberrant bone mass, including, but not limited to, osteoporosis, bone fractures, osteomyelitis, hypercalcemia and osteogenesis imperfecta. Also contemplated is the use of the methods described herein to identify molecules for the treatment of disorders of cholesterol, glucose, and/or fat metabolism such as diabetes mellitus, hypercholesterolemia, or obesity.

The term "analyte" includes molecule, compound, composition, drug, protein, peptide, nucleic acid, antibody and active fragment thereof, nucleic acid aptamer, peptide aptamer, and the like.

BRIEF DESCRIPTION OF THE DRAWINGS

FIG. 1 shows the nucleotide sequence of the rhesus monkey Dkk-cDNA, as set forth in SEQ ID NO:1. Nucleotide number is shown on the right. See EXAMPLES 5 and 6.

FIG. 2 shows the predicted amino acid sequence of the rhesus monkey Dkk-1 protein, as set forth in SEQ ID NO:2. Amino acid number is shown on the left.

FIG. 3A shows an alignment of the human and rhesus monkey Dkk-1 cDNA sequences (101 through 550). Nucleotides that are different between the two species are in bold.

FIG. 3B continues the alignment of the human and rhesus monkey Dkk-1 cDNA sequences of FIG. 3A. Nucleotides that are different between the two species are in bold.

FIG. 4 shows an alignment of the human, mouse, and rhesus monkey Dkk-1 predicted protein sequences. Dots indicate that spaces were added to facilitate alignment of the sequences.

DETAILED DESCRIPTION OF THE INVENTION

Figure 5:
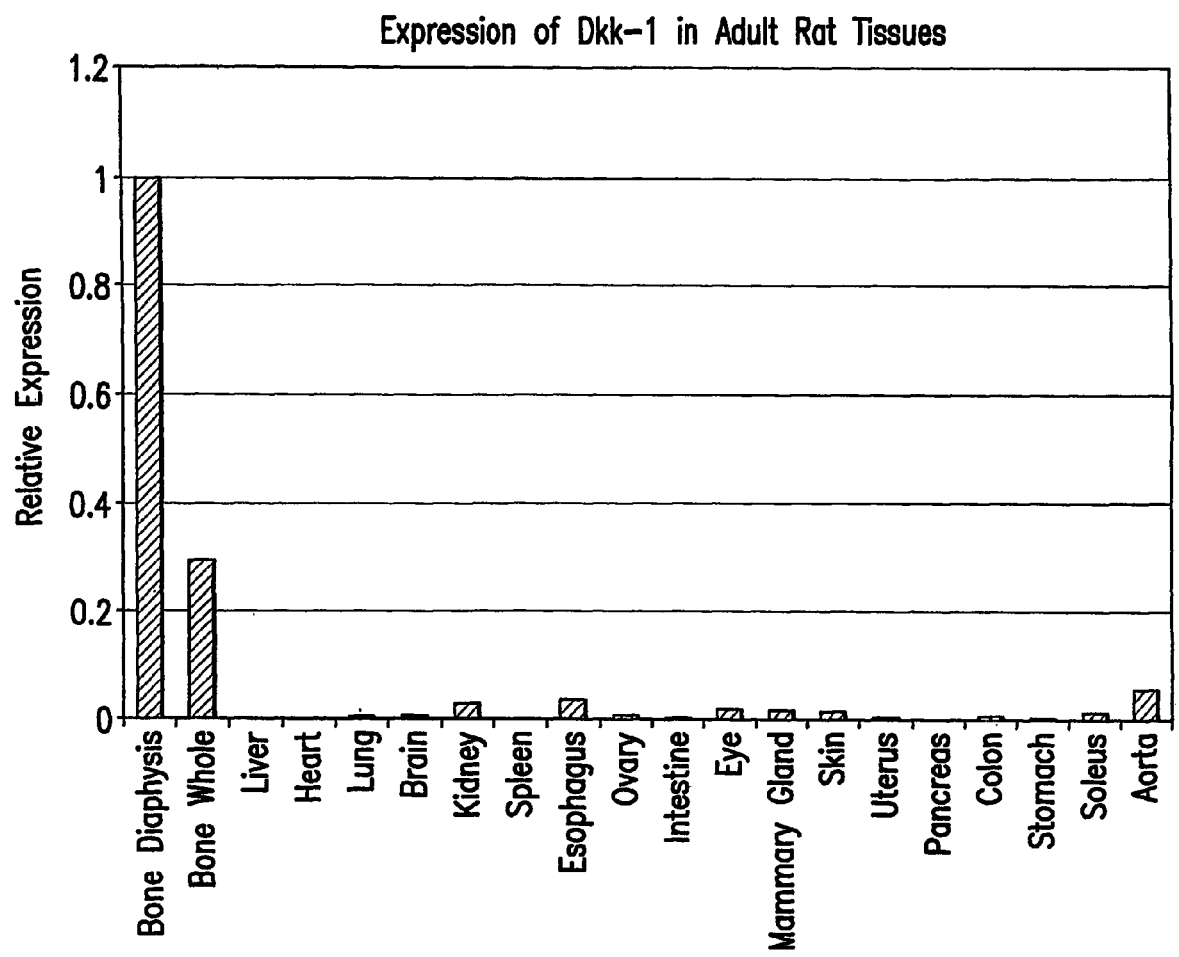
FIG. 5 shows the relative expression of Dkk-1 in adult rat tissues. Dkk-1 expression was determined by TaqMan-PCR as described in EXAMPLE 3.

Osteoporosis is characterized by bone loss resulting from an imbalance between bone resorption (destruction) and bone formation. This skeletal disorder often leads to morbidity and mortality among the elderly, due in part to insufficient estrogen levels. Finding novel treatments for osteoporosis is a leading health concern because traditional therapies, which act by preventing bone loss, are ineffective treatments for patients who have already suffered significant bone loss. The identification of molecular targets for the development of osteoanabolic treatments, which act by stimulating bone growth, would be an invaluable tool for drug discovery for the treatment of osteoporosis and other bone mass disorders.

The low-density lipoprotein receptor related protein 5 (LRP5) had been previously identified as a target for the development of osteoporosis therapeutics based on its genomic proximity to the osteoporosis pseudoglioma syndrome (OPG) locus and the observation that LRP5 loss-of-function mutations are associated with OPG (Hey et al., Gene 216: 103-111 (1998); Gong et al., Cell 107: 513-523 (2001)). In addition, Kato et al. (J. Cell Biol. 157: 303-314 (2002)) demonstrated that null mutations of LRP5 in mice resulted in severe bone loss, further indicating that LRP5 had a role in the maintenance of sufficient bone mass. It has been shown that LRP5 and its homologue LRP6 are activators of the Wingless (Wnt) signaling pathway and that the various Dickkopf (Dkk) proteins inhibit the Wnt signaling pathway by binding to LRP5 or LRP6. For example, Dkk-1 has been shown to inhibit Wnt signaling by directly binding LRP5 and LRP6 (Semenov et al., Curr. Biol. 11: 951-961 (2001); Bafico et al., Nat. Cell Biol. 3: 683-686 (2001)).

A role for LRP5 in glucose/lipid/fat metabolism was also disclosed in WO 98/46743 to Todd et al. which showed an LRP5 gene polymorphism in a patient with type I (insulin dependent) diabetes. This role is supported in Fujino et al., Proc. Natl. Acad. Sci. USA, 100: 229-34 (2003) which showed that LRP5 null mutation mice who are maintained on a high fat diet suffer from hypercholesterolemia and impaired glucose metabolism Hypercholesterolemia, impaired fat tolerance, and advanced atherosclerosis were also observed in LRP5 (−/−) mice who were also null for the Apo-lipoprotein E gene (Magoori et al., J. Biol. Chem. 278: 11331-36 (2003)). Interestingly, a recent report documented the negative regulatory role for Wnt signaling, a downstream mediator of LRP5 signaling, in adipogenesis (Bennett et al., J. Biol. Chem. 277: 30998-1004 (2002)). The above observations demonstrate a role for LRP5 and Wnt signaling in cholesterol, glucose, and fat metabolism in addition to their role in bone formation. Thus, the methods disclosed herein for identifying analytes which are modulators of Dkk-1 mediated signaling would also be useful for identifying analytes which could be used for treating disorders of cholesterol, glucose and fat metabolism, including, but not limited to, diabetes, hypercholesterolemia, and obesity.

Figure 6:
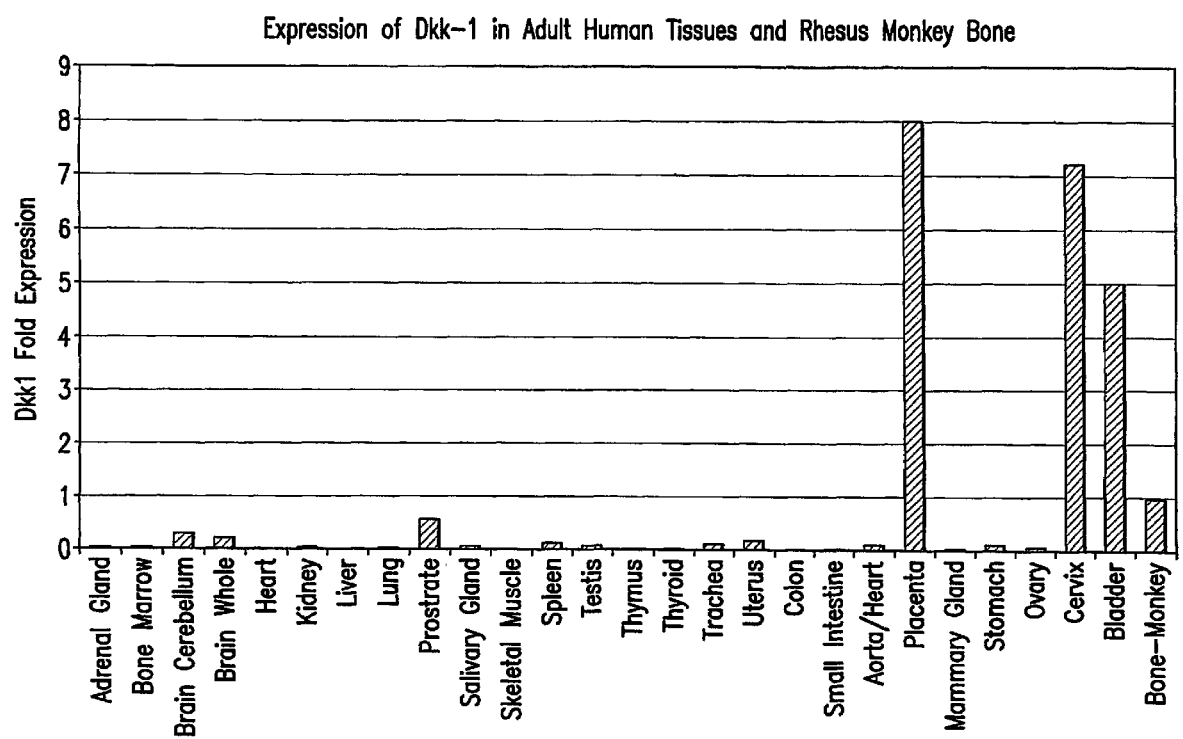
FIG. 6 shows the expression of Dkk-1 in adult human tissues and in rhesus monkey bone. Dkk-1 expression was determined by TaqMan-PCR as described in EXAMPLE 3.

It is shown herein that Dkk-1 is highly expressed in bone tissue. The expression profile of Dkk-1 in adult rat tissues was analyzed by TAQMAN PCR as described in Example 3. Parallel experiments performed using bone tissue from non-human primates as well as a panel of human tissues confirmed the expression of Dkk-1 in bone (FIG. 5). Dkk-1 was also found to be expressed in human prostate, placenta, cervix, and bladder (FIG. 6). The spatial expression patterns of Dkk-1 demonstrate a unique role for Dkk-1 as an antagonist for LRP5/6 signaling in bone. Thus, these observations, together with the association of LRP5 with human skeletal syndromes, provide additional evidence that Dkk-1 is a molecular target for novel osteoanabolic treatment.

The isolated cDNA clones, associated vectors, hosts, recombinant subcellular fractions and membranes, and the expressed and mature forms of rhDkk-1 are useful for the identification of analytes that interfere with or alter the molecular and/or functional interaction between Dkk-1 and one or more of its receptors including LRP5 or 6, kremen1, and kremen2. The analytes can be used in therapeutic pharmaceutical compositions for the osteoanabolic treatment of disorders involving bone loss such as osteoporosis and fracture repair. Bone formation is stimulated by treating a patient who has suffered bone loss with an analyte, which inhibits binding of Dkk-1 to LRP5, LRP6, kremen1, kremen2, or combinations thereof. By inhibiting binding of Dkk-1 to LRP5, LRP6, kremen1, kremen2, or combinations thereof, the Wnt signaling pathway is activated which in turn stimulates or increases bone formation in the patient. To identify analytes that stimulate bone formation, the isolated rhesus monkey Dkk-1 (rhDkk-1) protein is provided. The rhDkk-1 is used in methods for identifying analytes which stimulate bone formation by antagonizing the association of Dkk-1 to one or more Dkk receptors such as LRP5, LRP6, kremen1, kremen2 and combinations thereof. Pharmaceutical compositions identified by the methods of the present invention may be used alone or in combination with inhibitors of bone resorption such as bisphosphonates, estrogens, selective estrogen receptor modulators (SERMs) and calcitonin.

Non-limiting examples of methods for identifying such analytes include (i) cell-based binding methods for identifying analytes which inhibit or suppress binding between rhDkk-1 and one or more homologous or heterologous receptors such as LRP5, LRP5, kremen1, or kremen2 expressed in mammalian cells; (ii) cell-free binding methods for identifying analytes which inhibit or suppress binding between rhDkk-1 and one or more homologous or heterologous receptors such as LRP5, LRP6, kremen1, kremen2, or extracellular domain thereof; (iii) osteoblast differentiation methods for identifying analytes which inhibit or suppress Dkk-1 inhibition of differentiation of preosteoblastic cells; and, (iv) cell-based reporter methods for identifying analytes which inhibit or suppress rhDkk-1 inhibition of one or more homologous or heterologous receptors such as LRP5, LRP5, kremen1, or kremen2. Thus, the methods described herein are useful tools for identifying analytes which modulate molecular and/or functional interactions between rhDkk-1 and one or more homologous or heterologous receptors. In particular, the methods described herein are useful for identifying analytes which are suppressors or inhibitors of Dkk-1 expression or interfere with, suppress, or inhibit Dkk-1/receptor interactions and thus, are activators of the Wnt signaling pathway involved in bone formation, for use in treatments for disorders characterized by bone loss. Such disorders include, but are not limited to, osteoporosis and other disorders characterized by bone loss. Although not wishing to be bound by theory, the identified modulators are useful for stimulating or increasing bone formation because the modulators antagonize the association between Dkk-1 and one or more Dkk receptors in a manner which activates the Wnt pathway. The analytes identified by the methods of the present invention are also useful for treatment of disorders of cholesterol or fat metabolism such as obesity and diabetes.

The present invention is particularly useful for identifying analytes of pharmaceutical importance which can be used in designing therapies or treatments for osteoporosis and other disorders which are characterized by bone loss wherein the object of the therapy or treatment is to both inhibit or suppress the bone loss and to stimulate formation of bone tissue to replace that bone which had been lost. Therefore, in one aspect of the present invention, an isolated nucleic acid molecule is provided which comprises a sequence of nucleotides encoding an RNA molecule which can be translated in vivo or in vitro to produce the rhesus monkey Dkk-1 protein with the amino acid sequence as set forth in SEQ ID NO:2 (FIG. 2). In further embodiments, the nucleic acid is substantially free from other nucleic acids of the rhesus monkey or substantially free from other nucleic acids. In a further embodiment, the isolated nucleic acid molecule comprises the nucleotide sequence set forth in SEQ ID NO:1 (FIG. 1).

The isolated nucleic acid molecules include both deoxyribonucleic acid (DNA) and ribonucleic acid (RNA) molecules encoding the rhDkk-1 protein. The isolated nucleic acid molecules further include genomic DNA and complementary DNA (cDNA) encoding the rhDkk-1 protein, either of which can be single- or double-stranded, as well as synthetic DNA, such as a synthesized, single stranded polynucleotide. When single-stranded, the DNA molecule can comprise either the coding (sense) strand or the non-coding (antisense) strand. For most cloning purposes, DNA is a preferred nucleic acid. In the case of nucleic acid molecules isolated from genomic DNA, the nucleic acid sequences encoding the Dkk-1 protein can be interrupted by one or more introns.

In further aspects of the present invention, rhDkk-1 proteins are provided which have an amino acid sequence which is substantially similar to the amino acid sequence set forth SEQ ID NO:2 and nucleic acids which encode the rhDkk-1 proteins for use in the analyte screening assays disclosed herein. Further provided are nucleic acids encoding the rhDkk-1 protein which have a nucleotide sequence substantially similar to the nucleotide sequence set forth in SEQ ID NO:1. As used herein, the term "substantially similar" with respect to SEQ ID NO:2 means that the rhDkk-1 protein contains mutations such as amino acid substitution or deletion mutations which do not abrogate the ability of the rhDkk-1 protein to bind at least one of its receptors and suppress or inhibit Wnt signaling. The mutations include naturally occurring allelic variants and variants produced by recombinant DNA methods. As used herein, the term "substantially similar" with respect to SEQ ID NO:1 means that the rhDkk-1 protein encoded by the nucleic acid contains mutations such as nucleotide substitution or deletion mutations which do not abrogate the ability of the rhDkk-1 protein to bind at least one of its receptors and suppress or inhibit Wnt signaling. The mutations include naturally occurring allelic variants and variants produced by recombinant DNA methods. In general, any of the foregoing mutations which do not abrogate the ability of rhDKK-1 protein to bind at least one of its homologous or heterologous Dkk-1 receptors are conservative mutations.

The present invention further includes biologically active fragments or mutants of SEQ ID NO:1. Any such biologically active fragment and/or mutant will encode either a polypeptide or polypeptide fragment which at least substantially mimics the properties or activity of the rhDkk-1 protein, including but not limited to the rhDkk-1 protein as set forth in SEQ ID NO:2. Any such polynucleotide includes, but is not limited to, nucleotide substitutions, deletions, additions, amino-terminal truncations, and carboxy-terminal truncations which do not substantially abrogate the properties or activities of the rhDkk-1 protein produced therefrom. Thus, the mutations of the present invention encode mRNA molecules that express a rhDkk-1 protein in a eukaryotic cell which has sufficient activity (ability to bind one or more of its receptors) to be useful in drug discovery.

The present invention further includes synthetic DNAs (sDNA) which encode the rhDkk-1 protein wherein the nucleotide sequence of the sDNA differs from the nucleotide sequence of SEQ ID NO:1 but still encodes the rhDkk-1 protein as set forth in SEQ ID NO:2. For example, to express or enhance expression of the rhDkk-1 protein in a particular cell type, it may be necessary to change the sequence comprising one or more of the codons encoding the rhDkk-1 protein to sequences which enable expression of the rhDkk-1 protein in the particular cell type. Such changes include modifications for codon usage peculiar to a particular host or removing cryptic cleavage or regulatory sites which would interfere with expression of the rhDkk-1 protein in a particular cell type. Therefore, the present invention discloses codon redundancies which may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not alter or do not substantially alter the ultimate physical or functional properties of the expressed protein (in general, these mutations are referred to as conservative mutations). For example, substitution of valine for leucine, arginine for lysine, or asparagine for glutamine may not cause a change in the functionality of the polypeptide.

It is known that DNA sequences encoding a peptide may be altered so as to code for a peptide that has properties that are different than those of the naturally occurring peptide. Methods for altering the DNA sequences include, but are not limited to, site-directed mutagenesis. Examples of altered properties include, but are not limited to, changes in the affinity of an enzyme for a substrate or a receptor for a ligand.

Included in the present invention are DNA sequences that hybridize to SEQ ID NO:1 under stringent conditions. By way of example, and not limitation, a procedure using conditions of high stringency is as follows. Prehybridization of filters containing DNA is carried out for about 2 hours to overnight at about 65° C. in buffer composed of 6×SSC, 5× Denhardt's solution, and 100 µg/ml denatured salmon sperm DNA. Filters are hybridized for about 12 to 48 hrs at 65° C. in prehybridization mixture containing 100 µg/ml denatured salmon sperm DNA and 5-20×106 cpm of 32P-labeled probe. Washing of filters is done at 37° C. for about 1 hour in a solution containing 2×SSC, 0.1% SDS. This is followed by a wash in 0.1×SSC, 0.1% SDS at 50° C. for 45 minutes before autoradiography. Other procedures using conditions of high stringency would include either a hybridization step carried out in 5×SSC, 5× Denhardt's solution, 50% formamide at about 42° C. for about 12 to 48 hours or a washing step carried out in 0.2× SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, $3^{rd}$ Edition. Cold Spring Harbor Laboratory Press, Plainview, N.Y. (2001). In addition to the foregoing, other conditions of high stringency which may be used are also well known in the art.

In an another aspect of the present invention, a substantially purified form of a rhDkk-1 protein which comprises a sequence of amino acids as disclosed in FIG. 2 (SEQ ID NO:2) is provided. Further provided are biologically active fragments and/or mutants of the rhDkk-1 protein, which comprise at least a portion of the amino acid sequence set forth in SEQ ID NO: 2. These mutations or fragments include, but not limited to, amino acid substitutions, deletions, additions, amino terminal truncations, and carboxy-terminal truncations such that these mutations provide for proteins or protein fragments of diagnostic, therapeutic, or prophylactic use and are useful for screening assays for identifying analytes which interfere with the interaction of rhDkk-1 and one or more homologous or heterologous receptors, such analytes being useful for treatment of osteoporosis or other conditions characterized by aberrant bone mass and/or bone loss and treatment of disorders of cholesterol or fat metabolism such as obesity and diabetes. In a particular embodiment, the present invention provides an isolated nucleic acid molecule comprising a sequence which encodes a mutated rhDkk-1 protein comprising the sequence set forth in SEQ ID NO:2 with about 1-10 amino acid additions, deletions, or substitutions, wherein the mutated rhDkk-1 polypeptide binds at least a homologous or heterologous LRP5, preferably a human LRP5.

The rhDkk-1 proteins of the present invention can be the "mature" protein or a fragment or portion thereof, any of which can be a part of a larger protein such as a fusion protein. It is often advantageous to include covalently linked to the amino acid sequence of the rhDkk-1 protein, an additional amino acid sequence which contains secretory or leader sequences, pro-sequences, sequences which aid in purification of the rhDkk-1 proteins such as multiple histidine residues (polyHis) or antibody-binding epitopes, or one or more additional amino acid sequences which confer stability to the rhDkk-1 protein during recombinant production. Thus, rhDkk-1 fusion proteins are provided which comprise all or part of the rhDkk-1 protein linked at its amino or carboxyl terminus to proteins or polypeptides such as green fluorescent protein (GFP), c-myc epitope, alkaline phosphatase, protein A or G, glutathione S-transferase (GST), polyHis, peptide cleavage site, or antibody Fc region. Any such fusion construct can be expressed in a cell line of interest and used to screen for modulators of the rhDkk-1 protein disclosed herein. In a particular embodiment, the present invention provides an isolated nucleic acid molecule comprising a sequence which encodes a fusion rhDkk-1 protein comprising the sequence set forth in SEQ ID NO:2 or a fusion proteins with about 1-10 amino acid additions, deletions, or substitutions, wherein the mutated rhDkk-1 protein binds at least a homologous or heterologous LRP5, preferably a heterologous LRP5 such as a human LRP5.

The present invention further provides vectors which comprise at least one of the nucleic acid molecules disclosed throughout this specification, preferably wherein the nucleic acid molecule is operably linked to a heterologous promoter. These vectors can comprise DNA or RNA. For most cloning purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses the rhDkk-1 protein, polypeptide fragment thereof, or fusion protein comprising all or part of the rhDkk-1 protein encoded therein. It is well within the purview of the skilled artisan to determine an appropriate vector for a particular gene transfer or other use. As used herein, the term "recombinant Dkk-1 protein" is intended to include any variation of rhDkk-1 protein disclosed herein which is expressed from a vector transfected into a eukaryote cell or transformed into a prokaryote cell. Transfected eukaryote cells and transformed prokaryote cells are referred to as recombinant host cells.

An expression vector containing DNA encoding a rhDkk-1 protein or any one of the aforementioned variations thereof wherein the DNA is preferably operably linked to a heterologous promoter can be used for expression of the recombinant rhDkk-1 protein in a recombinant host cell. Such recombinant host cells can be cultured under suitable conditions to produce recombinant rhDkk-1 protein or a biologically equivalent form. Expression vectors include, but are not limited to, cloning vectors, modified cloning vectors, specifically designed plasmids, or specifically designed viruses.

Commercially available mammalian expression vectors which are suitable for recombinant rhDkk-1 protein expression include, but are not limited to, pcDNA3.neo (Invitrogen, Carlsbad, Calif.), pcDNA3.1 (Invitrogen), pcDNA3.1/Myc-His (Invitrogen), pCI-neo (Promega, Madison, Wis.), pLIT-MUS28, pLITMUS29, pLITMUS38 and pLITMUS39 (New England Bioalabs, Beverly, Mass.), pcDNAI, pcDNAIamp (Invitrogen), pcDNA3 (Invitrogen), pMC1neo (Stratagene, La Jolla, Calif.), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRS-Vgpt (ATCC 37199), pRSVneo (ATCC 37198), pSV2-dhfr (ATCC 37146), pUCTag (ATCC 37460), and 1ZD35 (ATCC 37565).

Also, a variety of bacterial expression vectors can be used to express recombinant rhDkk-1 protein in bacterial cells. Commercially available bacterial expression vectors which may be suitable for recombinant rhDkk-1 protein expression include, but are not limited to, pCR2.1 (Invitrogen), pET11a (Novagen, Madison, Wis.), lambda gt11 (Invitrogen), and pKK223-3 (Pharmacia).

In addition, a variety of fungal cell expression vectors may be used to express recombinant rhDkk-1 protein in fungal cells. Commercially available fungal cell expression vectors which are suitable for recombinant rhDkk-1 protein expression include, but are not limited to, pYES2 (Invitrogen) and *Pichia* expression vector (Invitrogen).

Also, a variety of insect cell expression vectors can be used to express recombinant rhDkk-1 protein in insect cells. Commercially available insect cell expression vectors which can be suitable for recombinant expression of rhDkk-1 protein include, but are not limited to, pBlueBacIII and pBlueBacHis2 (Invitrogen), and pAcG2T (Pharmingen).

Viral vectors which can be used for expression of recombinant rhDkk-1 protein include, but are not limited to, adenovirus vectors, adeno-associated virus vectors, herpesvirus vectors, Sindbis virus vectors, Simliki forest virus vectors, pox virus vectors (such as vaccinia virus, fowl pox, canary pox, and the like), retrovirus vectors, and baculovirus vectors. Many of viral vectors are commercially available.

The present invention further provides recombinant host cells transformed or transfected with a vector comprising any one of the aforementioned nucleic acid molecules, particularly host cells transformed or transfected with a vector comprising any one of the aforementioned nucleic acid molecules wherein the nucleic acid molecule is operably linked to a promoter. Recombinant host cells include bacteria such as *E. coli*, fungal cells such as yeast, plant cells, mammalian cells including, but not limited to, cell lines of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Also, mammalian species which may be suitable and which are commercially available, include but are not limited to, L cells L-M(TK-) (ATCC CCL-1.3), L cells L-M (ATCC CCL-1.2), Saos-2 cells (ATCC HTB-85), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-K1 cells (ATCC CCL-61), 3T3 cells (ATCC CCL-92), NIH/3T3 cells (ATCC CRL-1658), HeLa cells (ATCC CCL-2), C127I cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IFO50415), and CPAE cells (ATCC CCL-209). Such recombinant host cells can be cultured under suitable conditions to produce rhDkk-1 protein or a biologically equivalent form.

As noted above, an expression vector containing DNA encoding rhDkk-1 protein or any one of the aforementioned variations thereof can be used to express the rhDkk-1 protein encoded therein in a recombinant host cell. Therefore, the present invention provides a process for expressing a rhDkk-1 protein or any one of the aforementioned variations thereof in a recombinant host cell comprising introducing the vector comprising a nucleic acid which encodes the rhDkk-1 protein into a suitable host cell and culturing the host cell under conditions which allow expression of the rhDkk-1 protein. In a further embodiment, the rhDkk-1 protein has an amino acid sequence substantially as set forth in SEQ ID NO:2 and binds at least one homologous or heterologous Dkk-1 receptor such as LRP5, and the nucleic acid encoding the rhDkk-1 protein is operably linked to a heterologous promoter which can be constitutive or inducible. Thus, the present invention further provides a cell comprising a nucleic acid encoding the rhDkk-1 protein which has an amino acid sequence substantially as set forth in SEQ ID NO:2, which preferably binds at least one homologous or heterologous receptor such as LRP5, and wherein the nucleic acid encoding the rhDkk-1 protein is operably linked to a promoter.

The nucleic acids of the present invention are preferably assembled into an expression cassette that comprises sequences which provide for efficient expression of the rhDkk-1 protein or variant thereof encoded therein in a human cell. The cassette preferably contains the full-length cDNA encoding the rhDkk-1 protein or a DNA encoding a fragment of the rhDkk-1 protein with homologous or heterologous transcriptional and translational control sequences operably linked to the DNA. Such control sequences include at least a transcription promoter (constitutive or inducible) and transcription termination sequences and can further include other regulatory elements such as transcription enhancers, ribosome binding sequences, splice junction sequences, and the like. In most embodiments, the promoter is a heterologous promoter; however, in particular embodiments, the promoter can the natural rhDkk-1 promoter for ectopic expression of the rhDkk-1 in various host cells of non-rhesus monkey origin. In a particularly useful embodiment, the promoter is the constitutive cytomegalovirus immediate early promoter with or without the intron A sequence (CMV) although those skilled in the art will recognize that any of a number of other known promoters such as the strong immunoglobulin promoter, Rous sarcoma virus long terminal repeat promoter, SV40 small or large T antigen promoter, or the like. A preferred transcriptional terminator is the bovine growth hormone terminator although other known transcriptional terminators such as SV40 termination sequences can also be used. The combination of an expression cassette comprising the rhDkk-1 gene operably linked to the CMV promoter and the BGH terminator has been found to provide suitable expression of cDNA encoding the rhDkk-1 protein in eukaryote cells (See plasmid pcDNA3.1/Dkk-1/Myc-His-direct14 of Example 3).

Following expression of rhDkk-1 protein or any one of the aforementioned variations of the rhDkk-1 protein in a host cell, rhDkk-1 protein or variant thereof can be recovered to provide rhDkk-1 protein in a form capable of binding one or more homologous or heterologous Dkk receptors. Several rhDkk-1 protein purification procedures are available and suitable for use. The rhDkk-1 protein can be purified from cell lysates and extracts by various combinations of, or individual application of salt fractionation, ion exchange chromatography, size exclusion chromatography, hydroxylapatite adsorption chromatography, or hydrophobic interaction chromatography. In addition, rhDkk-1 protein can be separated from other cellular polypeptides by use of an immunoaffinity column made with monoclonal or polyclonal antibodies specific for rhDkk-1 protein or a particular epitope thereof. Alternatively, in the case of fusion polypeptides comprising all or a portion of the rhDkk-1 protein fused to a second polypeptide, purification can be achieved by affinity chromatography comprising a reagent specific for the second polypeptide such as an antibody or metal.

Cloning, expression vectors, transfections and transformations, and protein isolation of expressed proteins are well known in the art and have been described, for example, in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, $3^{rd}$ Edition. Cold Spring Harbor Laboratory Press, Plainview, N.Y. (2001). For example, any of a variety of procedures may be used to clone DNA encoding rhDkk-1 protein from RNA isolated from the rhesus monkey. These methods include, but are not limited to, the method shown in Examples 1-3 and the following methods.

(1) RACE PCR cloning methods such as disclosed in Frohman et al., Proc. Natl. Acad. Sci. USA 85: 8998-9002 (1988)). 5' and/or 3' RACE can be performed to generate a full-length cDNA sequence. This strategy involves using gene-specific oligonucleotide primers for PCR amplification of rhDkk-1 cDNA. These gene-specific primers are designed through identification of an expressed sequence tag (EST) nucleotide sequence which has been identified by searching any number of publicly available nucleic acid and protein databases.

(2) Direct functional expression of the rhDkk-1 cDNA following the construction of a rhDkk-1-containing cDNA library in an appropriate expression vector system.

(3) Screening a rhDkk-1-containing cDNA library constructed in a bacteriophage or plasmid shuttle vector with a labeled degenerate oligonucleotide probe designed from the amino acid sequence of the rhDkk-1 protein.

(4) Screening a rhDkk-1-containing cDNA library constructed in a bacteriophage or plasmid shuttle vector with a partial cDNA encoding the rhDkk-1 polypeptide. This partial cDNA is obtained by the specific PCR amplification of rhDkk-1 DNA fragments through the design of degenerate oligonucleotide primers from the amino acid sequence known for other membrane proteins which are related to the rhDkk-1 polypeptide.

(5) Screening a rhDkk-1-containing cDNA library constructed in a bacteriophage or plasmid shuttle vector with a partial cDNA or oligonucleotide with homology to a mammalian rhDkk-1 protein. This strategy may also involve using gene-specific oligonucleotide primers for PCR amplification of rhDkk-1 cDNA identified as an EST as described above.

(6) Designing 5' and 3' gene specific oligonucleotides using SEQ ID NO: 1 as a template so that either the full-length cDNA can be generated by known RACE techniques or a portion of the coding region can be generated by these same known RACE techniques to generate and isolate a portion of the coding region to use as a probe to screen one of numerous types of cDNA and/or genomic libraries in order to isolate a full-length version of the nucleotide sequence encoding rhDkk-1.

It would be readily apparent to those skilled in the art that other types of libraries, as well as libraries constructed from other cell types or species types, may be useful for isolating a rhDkk-1-encoding DNA or a rhDkk-1 homologue. Other types of libraries include, but are not limited to, cDNA libraries derived from other cells. The selection of cells or cell lines for use in preparing a cDNA library to isolate a cDNA encoding rhDkk-1 can be done by first measuring cell-associated rhDkk-1 activity using any known assay available for such a purpose.

Preparation of cDNA libraries can be performed by standard techniques well known in the art. Well known cDNA library construction techniques can be found for example, in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3$^{rd}$ Edition. Cold Spring Harbor Laboratory Press, Plainview, N.Y. (2001). Complementary DNA libraries may also be obtained from numerous commercial sources, including but not limited to Clontech Laboratories, Inc. (Palo Alto, Calif.) and Stratagene (La Jolla, Calif.).

The DNA molecules, RNA molecules, and recombinant polypeptides of the present invention can be used to screen and measure levels of rhDkk-1 expression in homologous or heterologous cells. The recombinant polypeptides, DNA molecules, and RNA molecules lend themselves to the formulation of kits suitable for the detection and typing of rhDkk-1 proteins. Such a kit would comprise a compartmentalized carrier suitable to hold in close confinement at least one container. The carrier would further comprise reagents such as recombinant rhDkk-1 or anti-rhDkk-1 antibodies suitable for detecting rhDkk-1 proteins. The carrier may also contain a means for detection such as labeled antigen or enzyme substrates or the like. The kit enables identification of polymorphic forms of rhDkk-1 protein which can then be used in the previously described methods to determine the effect the polymorphism has on binding between the polymorphic rhDkk-1 protein and a homologous or heterologous Dkk receptor and on the Wnt signaling pathway.

In accordance with yet another embodiment of the present invention, there are provided antibodies having specific affinity for the rhDkk-1 protein or epitope thereof. The term "antibodies" is intended to be a generic term which includes polyclonal antibodies, monoclonal antibodies, Fab fragments, single $V_H$ chain antibodies such as those derived from a library of camel or llama antibodies or camelized antibodies (Nuttall et al., Curr. Pharm. Biotechnol. 1: 253-263 (2000); Muyldermans, J. Biotechnol. 74: 277-302 (2001)), and recombinant antibodies. The term "recombinant antibodies" is intended to be a generic term which includes single polypeptide chains comprising the polypeptide sequence of a whole heavy chain antibody or only the amino terminal variable domain of the single heavy chain antibody ($V_H$ chain polypeptides) and single polypeptide chains comprising the variable light chain domain ($V_L$) linked to the variable heavy chain domain ($V_H$) to provide a single recombinant polypeptide comprising the Fv region of the antibody molecule (scFv polypeptides) (See, Schmiedl et al., J. Immunol. Meth. 242: 101-114 (2000); Schultz et al., Cancer Res. 60: 6663-6669 (2000); Dübel et al., J. Immunol. Meth. 178: 201-209 (1995); and in U.S. Pat. No. 6,207,804 B1 to Huston et al.). Construction of recombinant single $V_H$ chain or scFv polypeptides which are specific against an analyte can be obtained using currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. In further embodiments, the recombinant antibodies include modifications such as polypeptides having particular amino acid residues or ligands or labels such as horseradish peroxidase, alkaline phosphatase, fluors, and the like. Further still embodiments include fusion polypeptides which comprise the above polypeptides fused to a second polypeptide such as a polypeptide comprising protein A or G Invention antibodies can be produced by methods known in the art using invention polypeptides, proteins or portions thereof as antigens. For example, polyclonal and monoclonal antibodies can be produced by methods well known in the art, as described, for example, in Harlow and Lane, Antibodies: A Laboratory Manual (Cold Spring Harbor Laboratory (1988)). Invention polypeptides can be used as immunogens in generating such antibodies. Alternatively, synthetic peptides can be prepared (using commercially available synthesizers) and used as immunogens. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, e.g., Bahouth et al., Trends Pharmacol. Sci. 12:338 (1991); Ausubel et al., Current Protocols in Molecular Biology (John Wiley and Sons, N.Y. (1989)).

Antibodies so produced can be used for the immunoaffinity or affinity chromatography purification of the Dkk-1 polypeptide. The above referenced anti-Dkk-1 antibodies can also be used to modulate the activity of the Dkk-1 protein in living animals, in humans, or in biological tissues isolated therefrom. Accordingly, contemplated herein are compositions comprising a carrier and an amount of an antibody having specificity for Dkk-1 effective to block naturally occurring Dkk-1 from binding to its receptors, thereby modulating Wnt activity and stimulating bone growth.

Therefore, the nucleic acids encoding rhDkk-1 protein or variant thereof, vectors containing same, host cells transformed with the nucleic acids or vectors which express the rhDkk-1 protein or variants thereof, the rhDkk-1 protein and variants thereof, as well as antibodies specific for rhDkk-1 protein, can be used in in vivo or in vitro methods for screening a plurality of analytes to identify analytes which are modulators of the rhDkk-1 protein/receptor interaction. These methods provide information regarding the function and activity of the rhDkk-1 protein and variants thereof which can lead to the identification and design of molecule, compounds, or compositions capable of specific interactions with human Dkk-1 protein. In preferred embodiments, the methods identify analytes which interfere with the binding of the rhDkk-1 protein to a homologous or heterologous Dkk receptor involved in the Wnt signaling pathway, for example, LRP5 or 6, Kremen1 or 2, or combinations thereof. Thus, the methods identify analytes which inhibit or suppress Dkk-1 protein suppression of Wnt signaling. Such analytes are useful either alone or in combination with other compounds for treating osteoporosis and other disorders characterized by bone loss or treating disorders of cholesterol or fat metabolism such as obesity and diabetes.

Accordingly, the present invention provides methods (screening assays) for identifying analytes which modulate the binding of rhDkk-1 protein to one or more homologous or heterologous Dkk receptors (for example, LRP5, LRP6, kremen1 or kremen2). That is, screening method for identifying candidate or test compounds or agents, for example, peptides, peptidomimetics, small molecules or other drugs. Modulators can include, for example, agonists and/or antagonists. In a particularly preferred embodiment, the present invention provides methods for identifying analytes which modulate binding of rhDkk-1 protein to LRP5 and Kremen2.

As used herein, a compound or a signal that "modulates the activity" of rhesus Dkk-1 refers to a compound or a signal that alters the activity of rhDkk-1 so that the activity of the rhDkk-1 is different in the presence of the compound or signal than in the absence of the compound or signal. In particular, such compounds or signals include agonists and antagonists.

The term "agonist" refers to a substance or signal, such as Dkk-1, that activates receptor function; and the term "antagonist" refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

Methods for evaluating the modulating effects of a test substance on the interaction of Dkk-1 with its receptors are known in the art. In addition to the binding assays described below, other methods can be used for identifying molecules that modulate the interaction between rhDkk-1 and its receptors including other cell-based binding assays between Dkk-1 protein and LRP5, LRP6, kremen1 or kremen2. Such methods include, but are not limited to osteoblast differentiation assays in preosteoblastic cells and cell based reporter assays to detect Dkk-1 inhibition of LRP5/6 signaling.

In preferred embodiments, the screening methods disclosed herein are useful for identifying compounds that bind to the site or domain of rhDkk-1 that is involved in binding to a particular Dkk receptor or to a site or domain on the Dkk receptor which is involved in binding to the rhDkk-1 protein. The interference in binding can be measured directly by identifying the rhDkk-1 protein/Dkk receptor complex or indirectly by monitoring a downstream cellular response to the interference in binding such as activation of a reporter gene responsive to the interference in binding or a cellular marker that is expressed in cells induced to differentiate into osteoblasts.

In the various embodiments of the cell-based and cell-free methods disclosed herein, the Dkk receptor is preferably obtained from an organism selected from the group consisting of *Xenopus*, mouse, rat, and human. More preferably, the Dkk receptor is of human origin. The Dkk receptor is preferably selected from the group consisting of LRP5, LRP6, kremen1, and kremen2. For many of the methods disclosed herein, the preferred Dkk receptor is LRP5 or LRP6; however, some aspects can further include kremen1 or kremen2. Therefore, in a particularly preferred aspect, the method includes Dkk receptors LRP5 or LRP6 and Kremen1 and/or 2. In a particularly preferred aspect, the method includes LRP5 or 6 and Kremen2. Many cell-based methods can further include other components of the Wnt pathway such as Wnt protein, Dishevelled protein, and Frizzled protein. Vectors that express the human LRP5 receptor have been disclosed in U.S. Pat. No. 6,555,654 to Todd et al.; WO02/092015 to Allen et al.; Mao et al., Cell 107: 513-523 (2001); and, Mao et al., Mol. Cell 7: 801-809 (2001) and vectors that express the human LRP6 receptor are disclosed in Mao et al., Nature 411: 321-325 (2001). Particular methods further include expression vectors which express the Wnt protein. Wnt protein expression vectors have been disclosed in Mao et al., Cell 107: 513-523 (2001); Mao et al., Nature 411: 321-325 (2001); and Boyden et al., N. Eng. J. Med. 346: 1513-1521 (2002). Expression vectors which express kremen1 and kremen2 have been disclosed in Mao and Niehers, Gene 302: 179-183 (2003) and Mao et al., Nature 417: 664-667 (2002).

In preferred embodiments, the screening methods disclosed herein are useful for identifying analytes which bind to the site or domain of rhDkk-1 protein that is involved in binding to a particular Dkk receptor or to a site or domain on the Dkk receptor which is involved in binding to the rhDkk-1 protein. In either case, the screening methods identify analytes which interfere with the binding of rhDkk-1 protein to a Dkk receptor. The interference in binding can be measured directly by identifying the rhDkk-1 protein/Dkk receptor complex or indirectly by monitoring a downstream cellular response to the interference in binding such as activation of a reporter gene responsive to the interference in binding or a cellular marker that is expressed in cells induced to differentiate into osteoblasts.

In a preferred embodiment, the method identifies analytes which activate Wnt signaling by inhibiting or suppressing Dkk-1 protein binding to a homologous or heterologous Dkk receptor such as LRP5 or LRP6. In a further embodiment, the method identifies analytes which activate Wnt signaling by inhibiting or suppressing Dkk-1 protein binding to a homologous or heterologous Dkk receptor such as LRP5 or LRP6 in combination with homologous or heterologous kremen1 or kremen2. Methods for identifying analytes which modulate (interfere with, inhibit, suppress, or stimulate) binding of rhDkk-1 protein to one or more homologous or heterologous Dkk receptors (preferably, a heterologous Dkk receptor, most preferably a heterologous Dkk receptor of human origin) include (i) cell-based binding methods for identifying analytes which inhibit binding between rhDkk-1 protein and at least one homologous or heterologous Dkk receptor such as LRP5, LRP5, kremen1, or kremen2 expressed in mammalian cells; (ii) cell-free binding methods for identifying analytes which inhibit binding between rhDkk-1 and at least one homologous or heterologous Dkk receptor such as LRP5, LRP6, kremen1, kremen2, or extracellular domain thereof, (iii) cell-based osteoblast differentiation methods for identifying analytes which inhibit or suppress Dkk-1 protein inhibition of differentiation of preosteoblastic cells; and, (iv) cell-based reporter methods for identifying analytes which modulate rhDkk-1 protein inhibition of at least one Dkk receptor such as LRP5, LRP5, kremen1 or kremen2. The rhDkk-1 protein and the human Dkk-1 protein differ by 10 amino acids (See FIG. 4). Therefore, while the methods disclosed herein use the rhDkk-1 protein and nucleic acids encoding the same, the Dkk receptor (for example, LRP5, LRP6, kremen1, and kremen2) and nucleic acids encoding the same as well as other proteins and nucleic acids encoding proteins comprising the Wnt signaling pathway such as Wnt protein are not limited to those obtained from the rhesus monkey but can include those polypeptides and nucleic acids encoding the same from other mammals such as humans.

In one embodiment, the invention provides methods for screening a plurality of analytes for analytes which bind to or modulate the activity of rhDkk-1 protein or polypeptide or biologically active portion thereof. In another embodiment, the invention provides methods for screening a plurality of analytes for analytes which bind to or modulate the activity of a Dkk receptor. The plurality of analytes can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, Anticancer Drug Des. 12: 145 (1997)). Examples of methods for synthesizing molecular libraries can be found in the art, for example, DeWitt et al., Proc. Natl. Acad. Sci. USA 90: 6909 (1993); Erb et al., Proc. Natl. Acad. Sci. USA 91: 11422 (1994); Zuckermann et al., J. Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994).

Libraries of analytes can be presented in solution (for example, Houghten, Biotech. 13: 412-421 (1992)), or on beads (Lam, Nature 354: 82-84 (1991)), chips (Fodor Nature, 364: 555-556 (1993)), bacteria or spore (U.S. Pat. No. 5,223,409 to Ladner), plasmids (Cull et al., Proc Natl. Acad. Sci. USA 89: 1865-1869 (1992)) or on phage (Scott and Smith, Science 249: 386-390 (1990); Devlin, Science 249: 404-406 (1990); Cwirla et al., Proc. Natl. Acad. Sci. USA 87: 6378-6382 (1990); Felici J. Mol. Biol. 222:301-310(1991); and, U.S. Pat. No. 5,223,409 to Ladner).

In the various embodiments of the cell-based and cell-free methods disclosed herein, the Dkk receptor is preferably obtained from an organism selected from the group consisting of *Xenopus*, mouse, rat, and human. More preferably, the Dkk receptor is of human origin. The Dkk receptor is preferably selected from the group consisting of LRP5, LRP6, kremen1, and kremen2. In a particularly preferred method, the method includes Dkk receptors LRP5 and/or LRP6 and Kremen 1 and/or 2, in particular LRP5 and/or 6 and Kremen2. For many of the methods disclosed herein, the preferred Dkk receptor is LRP5 or LRP6; however, some methods can further include kremen1 or kremen2. Many cell-based methods can further include other components of the Wnt pathway such as Wnt protein, Dishevelled protein, and Frizzled protein. Vectors that express the human LRP5 receptor have been disclosed in U.S. Pat. No. 6,555,654 to Todd et al.; WO02/092015 to Allen et al.; Mao et al., Cell 107: 513-523 (2001); and, Mao et al., Mol. Cell 7: 801-809 (2001) and vectors that express the human LRP6 receptor are disclosed in Mao et al., Nature 411: 321-325 (2001). Particular methods further include expression vectors which express the Wnt protein. Wnt protein expression vectors have been disclosed in Mao et al., Cell 107: 513-523 (2001); Mao et al., Nature 411: 321-325 (2001); and Boyden et al., N. Eng. J. Med. 346: 1513-1521 (2002). Expression vectors which express kremen1 and kremen2 have been disclosed in Mao and Niehers, Gene 302: 179-183 (2003) and Mao et al., Nature 417: 664-667 (2002).

In one embodiment of a cell-based method, a recombinant cell which expresses a homologous or heterologous Dkk receptor on the cell surface is contacted with rhDkk-1 protein, to form a mixture. The mixture is then contacted with an analyte and the ability of the analyte to interact with a Dkk receptor is determined. The ability of the analyte to interact with a Dkk receptor comprises determining the ability of the analyte to preferentially bind to the Dkk receptor as compared to the ability of rhDkk-1 protein to bind to the receptor. In another embodiment, a recombinant cell expressing a homologous or heterologous Dkk receptor on the cell surface is contacted with a mixture comprising an analyte and rhDkk-1 protein and the ability of the analyte to interact with the Dkk receptor is determined. In a further still embodiment, a recombinant cell expressing a homologous or heterologous Dkk receptor on the cell surface is contacted with the analyte to form a mixture. The mixture is then contacted with the rhDkk-1 protein and the ability of the analyte to inhibit the rhDkk-1 protein from binding the Dkk receptor is determined.

Determining ability of the rhDkk-1 protein or the analyte to bind to the homologous or heterologous Dkk receptor on the cell surface can be accomplished by detecting the bound rhDkk-1 protein or analyte. For example, labeled antibodies specific for the rhDkk-1 protein or the analyte can be used to detect binding or the Dkk-1 protein or analyte can be labeled directly with a label. In further embodiments, the rhDkk-1 protein can be a fusion protein in which the amino or carboxyl terminus of the rhDkk-1 is covalently linked to a detectable polypeptide, including but not limited to, myc or an enzyme such as a alkaline phosphatase, which can be detected in a colorimetric assay or detectable protein such as Green fluorescent protein. Determining the ability of the rhDkk-1 protein to bind to a Dkk receptor in the presence of an analyte can also be accomplished by determining the activity of the receptor or an enzyme in a pathway responsive to the receptor. For example, the activity of the Dkk receptor can be determined by detecting induction of a cellular second messenger of the Dkk receptor (for example, intracellular $Ca^{2+}$, diacylglycerol, $IP_3$, alkaline phosphatase, and the like), detecting catalytic/enzymatic activity of the Dkk receptor on an appropriate substrate, detecting the induction of a reporter gene (comprising a Dkk-1 protein responsive regulatory element such as Wnt pathway inducible promoter such as the TCF binding sites operably linked to a nucleic acid encoding a detectable marker, for example, luciferase), or detecting a cellular response, for example, development, differentiation, or rate of proliferation.

Thus, in a particular embodiment, a cell-based binding method is provided which measures the ability of an analyte to modulate binding of rhDkk-1 protein to a homologous or heterologous Dkk receptor on the surface of a mammalian cell transfected with one or more expression vectors which expresses the Dkk receptor (for example, one or more expression vectors selected from the group consisting of vectors which express LRP5, LRP6, kremen1, and kremen2). The transfected cells are incubated in medium containing rhDkk-1 protein, preferably labeled with a reporter molecule such as alkaline phosphatase or a fluorescent dye, radioactive isotope, lanthanide such as europium, and an analyte. After incubation, the medium is removed and the cells treated with a reagent which detects the rhDkk-1 protein, for example a substrate and chromagen for detecting alkaline phosphatase activity, a labeled antibody specific for the rhDkk-1 protein, or appropriate light wavelength to induce the fluorescent dye or lanthanide to emit light. A lack of detectable signal from the reagent indicates that the analyte interferes with the ability of the rhDkk-1 protein to bind the Dkk receptor. Conversely, presence of detectable signal from the reagent indicates that the analyte has no apparent interfering effect on the ability of rhDkk-1 protein to bind the Dkk receptor. Cell binding methods which can be modified to use the rhDkk-1 protein are described in Mao et al., Nature 411: 321-325 (2001), Mao et al., Nature 417: 664-667 (2002).

By way of example, a suitable cell such the human HEK293T cell is transfected with one or more expression vectors, each of which expresses a Dkk receptor (for example, one or more expression vectors selected from the group consisting of vectors which express LRP5, LRP6, kremen1, and kremen2). Transfection can be performed using any one of transfection methods well known in the art, such methods including electroporation, LIPOFECTIN (Invitrogen), Calcium phosphate precipitation, DEAE-dextran, or FuGENE 6 (Roche Applied Sciences) and the transfected cells incubated for a time sufficient for expression of the Dkk receptor on the cell surface. In general, the transfected cells are incubated for about 48 hours at 37° C. and then incubated for about an hour at 37° C. in media containing rhDkk-1 protein fused at the carboxy terminus with a protein such as alkaline phosphatase for enzymatic detection or myc for immunological detection with labeled antibodies specific for the myc and the analyte being tested for its ability to inhibit or suppress binding of the rhDkk-1 to the receptor. In an alternative embodiment, the rhDkk-1 is labeled with a radioactive or fluorescent molecule or is unlabeled and detection of bound rhDkk-1 protein is via labeled antibodies against the rhDkk-1 protein. After incubating the cells containing rhDkk-1 protein, the cells are washed with a solution such as phosphate buffered saline and the cells reacted with a detection reagent suitable detecting the label. For example, the cells can be stained with Fast Red for detection of alkaline phosphatase label. The extent of inhibition or suppression of rhDkk-1 protein binding to the Dkk receptor on the cell surface is inversely proportional to the amount of detection reagent on the cell surface. Variations of the cell binding method which have the object of detecting inhibitors or suppressors of rhDkk-1 protein binding to a Dkk receptor on the cell surface are well within the purview of one of ordinary skill in the art.

In further embodiment of a cell-based method, modulators of Dkk-1 protein expression are identified by transfecting a cell with DNA encoding rhDkk-1 protein operably linked to its naturally occurring promoter or a heterologous promoter which directs expression of a rhDkk-1 protein (for example, the promoter which directs expression of the human Dkk-1 protein), contacting the transfected cell with an analyte, and measuring the expression of rhDkk-1 mRNA or protein in the cell. The level of expression of rhDkk-1 mRNA or protein in the presence of the analyte is compared to the level of expression of rhDkk-1 mRNA or protein in the absence of the analyte. The analyte can then be identified as a modulator of Dkk-1 protein expression based on this comparison. For example, when expression of rhDkk-1 mRNA or protein is greater (statistically significantly greater) in the presence of the analyte than in its absence, the analyte is identified as a stimulator of Dkk-1 mRNA or protein expression. Alternatively, when expression of rhDkk mRNA or protein is less (statistically significantly less) in the presence of the analyte than in its absence, the analyte is identified as an inhibitor of Dkk-1 mRNA or protein expression. The level of rhDkk-1 mRNA or protein expression in the cells can be determined by methods well known for detecting mRNA or proteins such as the methods described herein for detecting rhDkk-1 mRNA or protein. Expression of mRNA can be determined by RT-PCR, preferably a real-time RT-PCR method such as that provided by TAQMAN RT-PCR, or Northern blotting. Protein expression can be determined by Western blotting.

A further embodiment of a cell-based method for screening for analytes which interfere with binding of rhDkk-1 protein to a homologous or heterologous Dkk receptor is the two-hybrid system. The two-hybrid system is extremely useful for studying protein:protein interactions (See, Chien et al., Proc. Natl. Acad. Sci. USA 88: 9578-82 (1991); Fields et al., Trends Genetics 10: 286-92 (1994); Harper et al., Cell 75: 805-16 (1993); Vojtek et al., Cell 74: 205-14 (1993); Luban et al., Cell 73: 1067-78 (1993); Li et al., FASEB J. 7: 957-63 (1993); Zang et al., Nature 364: 308-13 (1993); Golemis et al., Mol. Cell. Biol. 12: 3006-14 (1992); Sato et al., Proc. Natl. Acad. Sci. USA 91: 9238-42 (1994); Coghlan et al., Science 267: 108-111 (1995); Kalpana et al., Science 266: 2002-6 (1994); Helps et al., FEBS Lett. 340: 93-8 (1994); Yeung et al., Genes & Devel. 8: 20879 (1994); Durfee et al., Genes & Devel. 7: 555-569 (1993); Paetkau et al., Genes & Devel. 8: 2035-45; Spaargaren et al., 1994 Proc. Natl. Acad. Sci. USA 91: 12609-13 (1994); Ye et al., Proc. Natl. Acad. Sci. USA 91: 12629-33 (1994); and U.S. Pat. Nos. 5,989,808; 6,251,602; and 6,284,519) and can be adapted to screen for analytes which interfere with binding of rhDkk-1 to one or more of its receptors.

The two-hybrid method relies upon the finding that the DNA binding and polymerase activation domains of many transcription factors, such as GAL4, can be separated and then rejoined to restore functionality (Morin et al., Nuc. Acids Res. 21: 2157-63 (1993)). While two-hybrid method is described with reference to the yeast system, it is understood that a two-hybrid screen can be conducted in other systems, for example systems which use prokaryote cells or mammalian cell lines.

An example of the two-hybrid method in yeast cells is as follows. Yeast strains with integrated copies of various reporter gene cassettes, such as for example GAL.fwdarw..LacZ, GAL.fwdarw.HIS3, or GAL.fwdarw.URA3 (Bartel, in Cellular Interactions and Development: A Practical Approach, 153-179 (1993); Harper et al., Cell 75: 805-16 (1993); Fields et al., Trends Genetics 10: 286-92 (1994)) are cotransformed with two plasmids, each expressing a different fusion protein. One plasmid encodes a fusion between rhDkk-1 protein and the DNA binding domain (DBD) of, for example, the DBD of the GAL4 yeast transcription activator (Brent et al., Cell 43: 729-36 (1985); Ma et al., Cell 48: 847-53 (1987); Keegan et al., Science 231: 699-704 (1986)), while the other plasmid encodes a fusion between a Dkk receptor such as LRP5 or cytoplasmic fragment thereof and the RNA polymerase activation domain (AD) of the same transcription factor, for example, the AD of the GAL4 (Keegan et al., supra). The plasmids are transformed into a strain of the yeast that contains a reporter gene cassette such as the lacZ, whose regulatory region contains GAL4 binding sites. If the rhDkk-1-DBD fusion protein is able to bind the Dkk receptor-AD fusion protein in the presence of a test analyte, they reconstitute a functional GAL4 transcription activator protein by bringing the two GAL4 components into sufficient proximity to activate transcription of the reporter gene. Thus, activation of transcription indicates that the analyte had no detectable effect on binding of rhDkk-1 protein to a Dkk receptor. However, if an analyte interferes with the ability of the rhDkk-1-DBD fusion protein to bind the Dkk receptor-AD fusion protein, the two GAL4 components are not brought into sufficient proximity to activate transcription of the reporter. Thus, no activation of transcription indicates that the analyte has an effect on rhDkk-1 protein binding to a Dkk receptor.

Either hybrid protein alone is unable to activate transcription of the reporter gene, the DNA-binding domain hybrid, because it does not provide an activation function, and the activation domain hybrid, because it cannot localize to the GALA binding sites. The reporter gene cassettes consist of minimal promoters that contain the GAL4 DNA recognition site (Johnson et al., Mol. Cell. Biol. 4: 1440-8 (1984); Lorch et al., J. Mol. Biol. 186: 821-824 (1984)) cloned 5' to their TATA box. Transcription activation of the reporter is scored by measuring either the expression of β-galactosidase or the growth of the transformants on minimal medium lacking the specific nutrient that permits auxotrophic selection for the transcription product, for example, URA3 (uracil selection) or HIS3 (histidine selection) (See, Bartel, Cellular Interactions and Development: A Practical Approach, 153-179 (1993); Durfee et al., Genes & Devel. 7: 555-569 (1993); Fields et al., Trends Genet. 10: 286-292 (1994); and U.S. Pat. No. 5,283,173).

Additional methods of preparing two-hybrid assay systems which are suitable for identifying analytes which interfere with binding of rhDkk-1 protein to a Dkk receptor would be evident to one of ordinary skill in the art (See for example, Finley et al. in The Yeast Two-Hybrid System (Bartel et al., eds., Oxford, 1997); Meijia Yang in The Yeast Two-Hybrid System (Bartel et al., eds., Oxford, 1997); Gietz et al., Mol. & Cell. Biochem. 172: 67-9 (1997); Young, Biol. Reprod. 58: 302-311 (1998); Brent et al., Annu. Rev. Genet. 31: 663-704 (1997)).

Another cell-based method for screening analytes to identify analytes which interfere with binding of rhDkk-1 protein to a homologous or heterologous Dkk receptor is a cell-based reporter assay. The cell-based reporter assay is a functional assay in which analytes are screened for the ability to activate a Wnt signaling pathway inhibited by rhDkk-1 protein. A reporter gene under the control of a promoter specifically activated by Wnt signaling (a promoter containing one or more Wnt signaling-responsive transcription control factor elements or binding sites). An example of a promoter containing Wnt signaling-responsive transcription binding sites is the leukocyte enhancer factor-1 (LEF-1) responsive promoter (See Hsu et al., Molec. Cell. Biol. 18: 4807-4818 (1998)). The LEF-1 responsive promoter is one of many promoters responsive to various transcription factors of the lymphoid enhancer factor-T cell factor (LEF/TCF) family. Reporter genes operably linked to the LEF-1 responsive promoter for studying protein interaction in the Wnt signaling pathway have been disclosed in Boyden et al., N. Eng. J. Med. 346: 1513-1521 (2002); Mao et al., Mol. Cell 7: 801-809 (2001); Hsu et al., Mol. Cell. Biol. 18: 4807-4818 (1998).

Reporter genes which are useful in the cell-based assays of the present invention include, but are not limited to, the β-galactosidase gene, β-lactamase gene, β-glucoronidase gene, Green fluorescent protein gene, and luciferase gene, each operably linked to a heterologous promoter which preferably contains one or more Wnt signaling-responsive transcription control factor elements or binding sites, particularly a promoter containing one or more elements responsive to one or more of the transcription factors of the LEF/TCF family.

A cell-based reporter assay which is exemplary comprises transfecting a suitable cell type such as one of those disclosed previously with expression vectors which separately express Wnt protein, LRP5 or LRP6, rhDkk-1 protein, LEF-1 transcription factor (LEF-1 protein), and reporter gene operably linked to a LEF-1 responsive promoter. Preferably each expression vector constitutively expresses its protein. For example, each nucleic acid is operably linked to the CMV promoter. The cells are incubated in medium containing an analyte. Inhibition or suppression of rhDkk-1 binding to LRP5 or LRP6 by the analyte is determined by activation of the Wnt signaling pathway which is measured by detecting expression of the reporter gene via the LEF-1 responsive reporter. In the absence of an analyte which inhibits or suppresses binding of rhDkk-1 to LRP5 or LRP6, the rhDkk-1 binds the LRP5 or LRP6. This prevents the LRP5 or LRP6 from binding the Wnt protein. The end result is that β-catenin does not form a complex with the LEF-1 protein and there is no activation of expression of the reporter gene via the LEF-1 responsive promoter. However, in the presence of an analyte which inhibits or suppresses binding of the rhDkk-1 to LRP5 or LRP6, the LRP5 or LRP6 binds the Wnt protein. The end result is that β-catenin forms a complex with the LEF-1 protein; the complex then activates expression of the reporter via binding to the LEF-1 responsive promoter. Controls comprise the above transfected cells incubated in medium not containing the analyte and vectors for normalizing transfection. Further embodiments of the cell-based reporter assay include providing expression vectors which express kremen1 or kremen2. Thus, the assay includes measuring reporter gene expression in cells transfected with the reporter gene expression vector and any combination of expression vectors selected from the group consisting of vectors which express LRP5, LRP6, Wnt, rhDkk-1, Dkk-1, kremen1, kremen2, and combinations thereof. For example, a combination of one or more vectors expressing rhDkk-1, LRP5, LRP6, Kremen1, and Kremen2. In particular, a combination of vectors including rhDkk-1, LRP5, LRP6, and Kremen2

A further still embodiment of a cell-based method for screening analytes to identify analytes which interfere with binding of rhDkk-1 to a homologous or heterologous Dkk receptor is an osteoblast differentiation assay in which analytes are screened to identify analytes which inhibit or suppress the inhibitory effect of rhDkk-1 on osteoblast differentiation. Katagiri et al., J. Cell Biol. 127: 1755-1766 (1994) and Yamaguchi et al., Biochem. Biophys. Res. Commun. 220: 366-371 (1996) have shown that adding exogenous growth factors to pluripotent marrow stromal cells induces the cells along an osteoblastic lineage. Gong et al. (Cell 107: 513-523 (2001) show that adding 300 ng/ml of BMP2 to the pluripotent mesenchymal cells C3H10T1/2 and ST2 results in expression of the osteoblastic markers alkaline phosphatase (ALP), Bglap, and Runx2. Gong et al. further show that ALP activity can be induced in C3H10T1/2 and ST2 cells by transfecting the cells with vectors expressing LRP5 and Wnt and that ALP activity can be induced in ST2 cells that are stably expressing LRP5 by transfecting the cells with a vector expressing Wnt. Thus, the Wnt signaling pathway is involved in differentiation of pluripotent cells along an osteoblast lineage. Therefore, because Dkk-1 and Dkk-1 can inhibit the Wnt signaling pathway by binding LRP5, the osteoblast differentiation assay of Gong et al. can be adapted to an assay which uses rhDkk-1 to identify analytes which inhibit or suppress Dkk-1 inhibition of osteoblast differentiation.

An osteoblast differentiation assay which is exemplary comprises transfecting pluripotent cells such as C3H10T1/2 or ST2 cells with expression vectors which separately express rhDkk-1, LRP5 or LRP6, and Wnt protein (for example, Wnt-1 or Wnt3 protein). The cells are incubated in medium containing the compound and induction of ALP in the presence of the analyte is determined. Detection of ALP activity indicates that the compound inhibits or suppresses binding of rhDkk-1 to the Dkk receptor. Controls comprise the above cells incubated in medium without the compound. Further embodiments include providing expression vectors which express kremen1 or kremen2 and transfecting the above cells with kremen1 or kremen2. Thus, the osteoblast differentiation assay includes measuring ALP activity in cells transfected with any combination of expression vectors selected from the group consisting of vectors which express LRP5, LRP6, Wnt, Dkk-1, kremen1, and kremen2.

In one embodiment of a cell-free screening method, the method is a competition assay in which the ability of an analyte to effectively compete with the rhDkk-1 protein for binding to a homologous or heterologous Dkk receptor is determined. Binding of the analyte can be determined either directly or indirectly. Binding can be determined using labeled or unlabeled antibodies against rhDkk-1 protein, analyte, or Dkk receptor, the rhDkk-1 protein-Dkk receptor complex, labeled rhDkk-1 protein or Dkk receptor, and combinations thereof. Labels include, but are not limited to, radioactive isotopes, fluorescent dyes, enzymatic reporters such as alkaline phosphatase or horseradish peroxidase, donor-quencher fluorescent dyes, antibody recognition sites such as those provided by fusion polypeptides (for example, rhDkk-1 protein fused to alkaline phosphatase or a myc antibody recognition sequence), lanthanides such as Europium.

In a further embodiment, the method includes contacting the Dkk-1 protein with a Dkk receptor which binds rhDkk-1 protein to form a mixture, adding an analyte to the mixture, and determining the ability of the analyte to interfere with the binding of the rhDkk-1 to the Dkk receptor. Further embodiments include providing any combination of Dkk receptor selected from the group consisting of LRP5, LRP6, kremen1, kremen2, and combinations thereof, preferably, LRP5 or LRP6. In a further embodiment, the a combination of LRP5 and LRP6 together with Kremen1 and Kremen2 is provided. Immunoprecipitation is a particular type of cell-free method which is useful for identifying analytes which inhibit binding of rhDkk-1 protein to one or more Dkk receptors.

In another embodiment of a cell-free method, the rhDkk-1 protein is contacted with an analyte and the ability of the analyte to inhibit or suppress subsequent binding of the rhDkk-1 protein to a homologous or heterologous Dkk receptor is determined. Determining the ability of the analyte to inhibit or suppress binding of the rhDkk-1 protein can be detected as discussed above for cell-based methods. Determining the ability of the rhDkk-1 protein to bind to a Dkk receptor can also be accomplished using a technology such as real-time Biomolecular Interaction Analysis (BIA) (Sjolander and Urbaniczky, Anal. Chem. 63: 2338-2345 (1991) and Szabo et al., Curr. Opin. Struct. Biol. 5: 699-705 (1995)). As used herein, "BIA" is a technology for studying biospecific interactions in real time, without labeling any of the interactants (for example, BIACORE). Changes in the optical phenomenon surface plasmon resonance (SPR) can be used as an indication of real-time reactions between biological molecules.

In many drug screening programs which screen libraries of analytes (drug, compounds, natural extracts, compositions, and the like), high throughput assays are desirable in order to maximize the number of analytes surveyed in a given period of time. Assays which are performed in cell-free systems, such as can be derived with purified or semi-purified proteins, are often preferred as "primary" screens in that they can be generated to permit rapid development and relatively easy detection of an alteration in a molecular target which is mediated by an analyte. Moreover, the effects of cellular toxicity and/or bioavailability of the analyte can be generally ignored in the in vitro system, the assay instead being focused primarily on the effect of the analyte on the molecular target as may be manifest in an alteration of binding affinity with upstream or downstream elements. Accordingly, in an exemplary screening method of the present invention, an analyte is contacted with rhDkk-1 protein or a Dkk receptor. The Dkk-1 protein or Dkk receptor can be soluble, on a membrane surface, or immobilized on a solid substrate such as the surface of the wells of microtiter plate, bioassay chip, or the like. To the mixture of the analyte and the rhDkk-1 protein or Dkk receptor is then added a composition containing a Dkk receptor or rhDkk-1 protein, respectively. Detection and quantification of complexes of rhDkk-1 protein and Dkk receptors in the presence of the analyte provide a means for determining an analyte's efficacy at inhibiting (or potentiating) complex formation between rhDkk-1 protein and a Dkk receptor. The efficacy of the analyte can be assessed by generating dose response curves from data obtained using various concentrations of the test compound. Moreover, a control can also be performed to provide a baseline for comparison. For the control, isolated and purified rhDkk-1 protein or Dkk receptor is added to a composition containing the Dkk receptor or rhDkk-1 protein and the formation of a rhDkk-1/Dkk receptor complex is quantified in the absence of the analyte.

The cell-free methods herein are amenable to use of both soluble and/or membrane-bound forms of isolated proteins (for example, rhDkk-1 protein or biologically active portions thereof or Dkk receptors). In the case of cell-free methods in which a membrane-bound form an isolated protein is used (for example, a Dkk receptor) it can be desirable to use a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON X-100, TRITON X-114, THESIT, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In particular embodiments of the above cell-free methods, it can be desirable to immobilize either rhDkk-1 protein or a Dkk receptor to facilitate separation of rhDkk-1 protein-Dkk receptor complexes from free rhDkk-1 protein and Dkk receptor, as well as to accommodate automation of the method. Binding of analyte to rhDkk-1 protein, or interaction of a rhDkk-1 protein with a homologous or heterologous Dkk receptor in the presence and absence of an analyte, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/rhDkk-1 fusion proteins or glutathione-S-transferase/Dkk receptor can be adsorbed onto glutathione SEPHAROSE beads (Sigma Chemical, St. Louis, Mo.) or glutathione-derivatized microtitre plates, which are then combined with the analyte or the analyte and either the non-adsorbed Dkk receptor or rhDkk-1 protein, and the mixture incubated under conditions conducive to complex formation (for example, at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix and the level of rhDkk-1 protein binding or activity determined using standard techniques.

Other methods for immobilizing proteins on matrices can also be used in the cell-free screening methods. For example, either rhDkk-1 protein or a Dkk receptor can be immobilized using a conjugation of biotin and streptavidin. Biotinylated protein or target molecules can be prepared from biotin-NHS (N-hydroxy-succinimide) using techniques well known in the art (for example, the biotinylation kit available from Pierce Biotechnology, Rockford, Ill.), and immobilized in the wells of streptavidin-coated 96 well plates (Pierce Biotechnology). Alternatively, antibodies reactive with Dkk-1 protein or Dkk receptor but which do not interfere with binding of the rhDkk-1 protein to a Dkk receptor can be derivatized to the wells of the plate, and unbound Dkk receptor or rhDkk-1 protein trapped in the wells by antibody conjugation. Methods for detecting such complexes, in addition to those described above for the GST-immobilized complexes, include immunodetection of complexes using antibodies reactive with the rhDkk-1 protein or Dkk receptor, as well as enzyme-linked assays which rely on detecting an enzymatic activity associated with the rhDkk-1 protein or Dkk receptor.

A further embodiment of a cell-free binding method for identifying analytes which inhibit binding of rhDkk-1 protein to one or more Dkk receptors such as those Dkk receptors selected from the group consisting of LRP5, LRP6, kremen1, kremen2, and combinations thereof, preferably, LRP5 or LRP6, or LRP5 or LRP6 and kremen2 is a modification of the GST fusion pull-down assay. The GST fusion pull-down assay has been described in Sambrook and Russell, Molecular Cloning: A Laboratory Manual 3$^{rd}$ Edition. Cold Spring Harbor Laboratory Press: Plainview, N.Y. (2001). A GST pull-down kit is available from Pierce Biotechnology. In the modified GST fusion pull-down assay used herein, either the DNA encoding rhDkk-1 protein or Dkk receptor is cloned in-frame with the GST of a pGEX vector (Amersham Pharmacia Bioscience, Piscataway, N.J.) and expressed as a GST fusion protein in the BL21 E. coli. The expressed GST fusion protein is bound to immobilized reduced glutathione support. Preferably, the immobilized glutathione support is provided as a column. Labeled Dkk receptor or rhDkk-1 protein (labeled protein), respectively, is incubated with the bound GST fusion protein in the presence of an analyte. Afterwards, unbound labeled protein is removed and the GST fusion protein bound or unbound to the labeled protein is eluted from the support with imidazole. The amount of labeled protein bound to the eluted GST fusion protein is determined by detecting the label. If the analyte interferes with rhDkk-1 binding to the Dkk receptor, there will little or no detectable labeled protein eluted with the GST fusion protein compared to controls without the analyte. Conversely, if the analyte does not interfere with rhDkk-1 binding to the Dkk receptor, the amount of labeled protein eluted with the GST fusion protein will be similar to the amount eluted in controls without the analyte.

The molecules identified in accordance with the method described above may be administered for the treatment or prevention of osteoporosis or other disorders related to aberrant bone mass in any mammal, preferably a human. The activation of Dkk-1 can be modulated by contacting the polypeptides with an effective amount of at least one compound identified by the above-described bioassays.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples are intended to promote a further understanding of the present invention without limiting the scope of the invention.

EXAMPLE 1

RNA Isolation from Bone

Molecular procedures were performed following standard procedures well known in the art (See, e.g., Ausubel et. al. Short Protocols in Molecular Biology, F.M., -2$^{nd}$. ed., John Wiley & Sons, (1992) and Sambrook et al., Molecular Cloning, A Laboratory Manual, 2$^{nd}$ ed., Cold Spring Harbor Laboratory Press (1989)).

RNA was isolated from tibia using the PURESCRIPT RNA Isolation Kit (Gentra Systems, Inc., Minneapolis, Minn.).

For initial tissue preparation, the diaphysis was dissected from rat tibia Tibia was isolated from rat bone and the metaphysis part was quickly removed. The diaphysis of the bone was then separated from the surrounding muscle. The bone marrow was then washed out with 0.9% sodium chloride solution with a syringe and needle. Tibia diaphysis was frozen in liquid nitrogen and stored at −70 to −80° C.

For cell lysis, four rat tibia (or half of monkey tibia) were smashed between two metal blocks covered with aluminum foil. The resulting powder was transferred immediately into a 50 mL centrifuge tube containing 20 mL cell lysis solution and mixed by inverting 3 times. The solution was homogenized quickly using tissue homogenizer PT 10/35 with generator PTA 10TS.

To precipitate proteins and DNA, 6.7 mL of protein-DNA precipitation solution was added to the lysate. The solution was mixed by inverting the tube 10 times and the tube was placed on ice for 15 minutes. After the 15 minute incubation on ice, the tube was centrifuged at 8,000 rpm (10,000×g) for 15 minutes. The precipitated proteins and DNA formed a tight pellet, allowing removal of the RNA-containing supernatant.

For RNA precipitation, the supernatant was poured into a clean 50 mL centrifuge tube containing 20 mL 100% isopropanol. The sample was mixed by inverting gently 50 times and incubated at room temperature for 10 minutes. Thereafter, the solution was centrifuged at 8,000 rpm (10,000×g) for 10 minutes to pellet the RNA. Most of the supernatant was poured off and the pellet with residual supernatant were transferred into a centrifuge tube. The sample was then centrifuged at 14,000×g for 5 minutes. The supernatant was removed with a pipette and the RNA pellet was washed several times with 70% ethanol. After the wash step, the RNA pellet was air dried for 5-10 minutes.

For RNA hydration, 0.1 mL RNase-free water was added to the pellet and allowed to rehydrate at room temperature for 10 minutes. The sample was mixed by pipetting up and down several times.

In order to remove residual DNA from the RNA isolated from bone, an on-column DNase digestion was performed using the RNEASY Mini Kit and the RNase-Free DNase Set (Qiagen, Hilden, Germany) according to the manufacturer's instructions.

EXAMPLE 2

Oligonucleotide Primers and Probes for TAQMAN PCR

Each of the oligonucleotide fluorescent probes were 5'-labeled with 6-carboxy-fluorescein (FAM) and were 3'-labeled with TAMRA. The specific sequences of primers and probes used to study expression of the dickkopf-1 transcript are listed below:

Rat Dkk-1:

```
                                          (SEQ ID NO:3)
    Forward       GGTCTGGCTTGCAGGATACAG (SEQ ID NO:4)
    Reverse       TGGTTTTAGTGTCTCTGGCAGGT (SEQ ID NO:5)
    Probe         CCATCAAACCAGCAATTCTTCCAGGC
```

Human Dkk-1:

```
                             (SEQ ID NO:6)
Forward      AGTACCAGACCATTGACAACTACCAG (SEQ ID NO:7)
Reverse      GGGACTAGCGCAGTACTCATCAG (SEQ ID NO:8)
Probe        TACCCGTGCGCAGAGGACGAGG
```

Rhesus Monkey Dkk-1:

```
                             (SEQ ID NO:9)
Forward      GAAGGTCAAGTGTGTACCAAGCATAG (SEQ ID NO:10)
Reverse      AAGTGTGAAGCCTAGAAGAATTACTGG (SEQ ID NO:11)
Probe        TTGATGGTGATCTTTCTGTATCCGGCAAG
```

EXAMPLE 3

Analysis of Dkk-1 Expression by TAQMAN PCR

Previous in situ hybridization by Glinka et al. (*Nature* 391: 357-362 (1998)) revealed that mouse and *Xenopus* Dkk-1 is expressed in embryonic tissues that contain head organizer activity, suggesting an important role for Dkk-1 in head induction. Consistent with the Glinka study, Krupnick and colleagues (Gene 238: 301-313 (1999)) detected Dkk-1 expression in placenta, but not in other tissues tested. To determine more precisely the expression profile of Dkk-1 in human adult tissues, as well as the expression of Dkk-1 in adult rat tissues and non-human primate bone tissue, TAQ-MAN PCR was performed using TAQMAN Reverse Transcription Reagents from Applied Biosystems (Foster City, Calif.).

To perform the reverse transcription step, total RNA samples were reverse transcribed in a GENEAMP PCR System 9700 (Applied Biosystems, Foster City, Calif.). A reverse transcription (RT) master mix containing all of the components of the RT-PCR reaction except the template RNA was prepared. The RT master mix was prepared by mixing the following components for each reaction: 1 µl of 10×RT buffer, 2.2 µl of 25 mM MgCl$_2$, 2 µl of 10×dNTP mix, 0.5 µl of random hexamers, 0.2 µl of RNAse inhibitor, 2.85 µl H$_2$O, and 0.25 µl MULTISCRIBE reverse transcriptase.

For each RNA sample, 1.1 µl RNA (diluted to a concentration of 75 ng/µl) was mixed with 9.9 µl RT master mix in separate 0.5 mL tubes (for negative control RT master mix was mixed with water). 10 µl aliquots of RT master mix+RNA were added into appropriate wells of a MICROAMP Optical 96-Well Reaction Plate and capped. The 96-well plate was transferred to the thermal cycler block of the GENEAMP PCR System 9700 and the samples were incubated at 25° C. for 10 min, followed by 30 min at 48° C., and 5 min at 94° C.

Following reverse transcription, the resulting cDNA templates were PCR-amplified using the TAQMAN PCR Core Reagent Kit (Applied Biosystems, Foster City, Calif.). A PCR master mix was prepared by mixing the following components for each reaction: 5 µl of 10× TAQMAN buffer A, 11 µl of 25 mM MgCl$_2$, 0.5 µl of EMPERASE UNG, 1 µl each of 10 mM dATP, 10 mM dCTP, 10 mM dGTP, 10 mM dUTP, primers, 10 µM probe and AMPLITAQ Gold enzyme and water to a total volume of 40 µl/well. 40 µl aliquots of this master mix was added to each well containing the cDNA templates. PCR was carried out in an ABI PRISM® 7700 Sequence Detection Systems Instrument (Applied Biosystems, Foster City, Calif.). The cycling conditions consisted of an initial step of 50° C. for 2 min followed by 95° C. for 10 min (denaturation), and 40 cycles of 95° C. for 15 sec (denaturation) and 60° C. for 1 min (annealing/extension).

Included in the Taq-Man PCR master mix was dUTP (instead of dTTP) and uracil-N-glycosylase (UNG), an enzyme that is activated at 50° C. and cleaves uracil-containing nucleic acids. See Longo et al., *Gene* 93: 125-128 (1990). UNG prevents the reamplification of carryover PCR products in subsequent experiments.

TAQMAN analysis of RNA isolated from adult rat tissues revealed that Dkk-1 is highly and selectively expressed in bone tissue. A similar analysis of bone tissue of human tissues confirmed the expression of Dkk-1 in bone. Dkk-1 was also expressed in human prostate, placenta, cervix and bladder. This expression pattern suggests a unique role for Dkk-1 as an antagonist for LRP5/6 signaling in bone.

EXAMPLE 4

Design of Oligonucleotide Primers for Dkk-1 Cloning

In order to design rhesus-specific primers for cloning Dkk-1, the 5'- and 3'-ends of the rhesus dicckopf-1 gene were sequenced first. RNA was extracted from rhesus monkey tibia using the PURESCRIPT RNA Isolation Kit (Gentra Systems, Minneapolis, Minn., see EXAMPLE 1) followed by On-Column DNase Digestion (Qiagen, Hilden, Germany). Resulting total RNA from bone was reverse transcribed using the Superscript First-Strand cDNA Synthesis Kit (Invitrogen, Carlsbad, Calif.) following the manufacturer's protocol. 2 µl of the resulting cDNA templates were amplified in a 50 µl PCR reaction containing the following components: 1×PCRx amplification buffer, 1×PCRx enhancer solution (Invitrogen), 1.5 mM MgSO$_4$, 200 uM each dNTP, 500 nM Forward and Reverse Primers and 2.5 U AMPLITAQ DNA polymerase (Applied Biosystems).

To isolate a fragment from the 5' end of Dkk-1 gene by PCR, the following oligonucleotide primers, designed from the Dkk-1 human nucleotide sequence, were used: 5'hDkk-1Forward, 5'-TCTCCCTCTTGAGTCCTTCTGAGATG-3' (SEQ ID NO:12), and 5'hDkk-1 Reverse, 5'-CGTTGGAAT-TGAGAACCGAGTTC A-3' (SEQ ID NO:13). To PCR-amplify a 3' Dkk-1 fragment, the following primers, which were also designed from the human sequence, were used: 3'hDkk-1Forward, 5'-GTCAT CAGACTGTGCCTCAGGATTG-3' (SEQ ID NO:14), and 3'hDkk-1Reverse, 5'-GAGTTCACT-GCATTTGGATAGCTGGT-3' (SEQ ID NO:15). The specific PCR cycling conditions consisted of an initial 6 min denaturation at 94° C., followed by 35 cycles of 94° C. for 1 min, 60° C. for 1 min and 72° C. for 2 min. The resulting PCR products were sequenced on an ABI 310 Genetic Analyzer using BIG-DYE Terminator chemistry (Applied Biosystems).

EXAMPLE 5

Sequencing of the Dickkopf-1 Gene from Rhesus Monkey

In order to obtain the entire coding sequence of the rhesus dickkopf-1 gene, rhesus bone cDNA (see EXAMPLE 3) was used to amplify fragments containing exons 1 and 2 and exons 2, 3, and 4 of the Dkk-1 gene. PCR was performed as described above (see EXAMPLE 3) using the following two primer pairs: 5'hDkk-1Forward, (SEQ ID NO:12) and hDkk-1R3,5'-GCACTGATGAGTACTGCGCTAGTC-3' (SEQ ID NO:16), and hDkk-1F3,5'-CACATAGCGTGACGCAT-GCA-3' (SEQ ID NO:17), and 3'hDkk-1Reverse (SEQ ID NO:15).

The resulting Dkk-1 fragments were sequenced on an ABI 310 Genetic Analyzer using BIGDYE Terminator chemistry (Applied Biosystems).

The complete nucleotide sequence for rhesus monkey Dkk-1 is shown in FIG. 1, herein set forth as SEQ ID NO:1. The predicated amino acid sequence corresponding to the rhesus Dkk-1 protein is shown in FIG. 2, herein set forth as SEQ ID NO:2.

EXAMPLE 6

Dickkopf-1 Cloning from Rhesus Monkey

After obtaining the rhesus Dkk-1 sequence, the following primers were designed to clone the entire coding sequence of the rhesus Dkk-1 gene: rhDkk1EcoRI-F, 5'-CGGAATTCAC-CATGATGGCTCTGGGCGCAGCAGGA-3' (SEQ ID NO:18, specific for monkey sequence), and hDkk1EcoRI-R, 5'-CGGAATTCGTG TCTCTGACAAGTGTGAAGCCTA-GAAGA-3' (SEQ ID NO:19, specific for monkey and human sequences). Using these primers, rhesus bone cDNA was PCR-amplified in a 50 µl reaction containing 1×Pfu Ultra HF Buffer, 200 uM each dNTP, 200 nM each primer and 2.5 U of Pfu Ultra HF DNA Polymerase (Stratagene, La Jolla, Calif.). The cycling conditions consisted of an initial 6 min denaturation at 94° C., followed by 32 cycles of 94° C. for 1 min, 60° C. for 1 min and 72° C. for 2 min.

The resulting 796 bp PCR product was digested with the EcoRI restriction endonuclease and ligated into EcoRI digested pcDNA3.1/Myc-His vector (Life Technologies, Carlsbad, Calif.). The ligation mix was used to transform MAX Efficiency DH5α Competent Cells (Life Technologies). Twenty colonies obtained from transformation were screened for the presence of insert and for the insert orientation using HindIII digestion and RFLP analysis. Based on this screening, a clone was selected that contained the Dkk-1 gene in the correct orientation. Sequencing of both strands of the selected clone on an ABI 310 Genetic Analyzer using BIG-DYE Terminator chemistry (Applied Biosystems) confirmed the presence of the Dkk-1 sequence. The plasmid from the selected clone is designated pcDNA3.1/rhDkk1/Myc-His-direct14.

EXAMPLE 6

This example describes a method for making polyclonal antibodies specific for the rhDkk-1 protein.

RhDkk-1 protein is produced in *E. coli* transformed with pcDNA3.1/rhDkk-1/Myc-His-direct14. Antibodies are generated in New Zealand white rabbits over a 10-week period. The rhDkk-1 protein is emulsified by mixing with an equal volume of Freund's complete adjuvant and injected into three subcutaneous dorsal sites for a total of 0.1 mg rhDkk-1 protein per immunization. A booster containing about 0.1 mg rhDkk-1 emulsified in an equal volume of Freund's incomplete adjuvant is administered subcutaneously two weeks later. Animals are bled from the articular artery. The blood is allowed to clot and the serum collected by centrifugation. The serum is stored at −20° C.

For purification, rhDkk-1 protein is immobilized on an activated support. Antisera is passed through the sera column and then washed. Specific antibodies are eluted via a pH gradient, collected, and stored in a borate buffer (0.125 M total borate) at −0.25 mg/mL. The anti-rhDkk-1 antibody titers are determined using ELISA methodology with free rhDkk-1 bound in solid phase (1 pg/well). Detection is obtained using biotinylated anti-rabbit IgG, HRP-SA conjugate, and ABTS.

EXAMPLE 7

This example describes a method for making monoclonal antibodies specific for the rhDkk-1 protein.

BALB/c mice are immunized with an initial injection of about 1 µg of purified rhDkk-1 protein per mouse mixed 1:1 with Freund's complete adjuvant. After two weeks, a booster injection of about 1 µg of the antigen is injected into each mouse intravenously without adjuvant. Three days after the booster injection serum from each of the mice is checked for antibodies specific for the rhDkk-1 protein.

The spleens are removed from mice positive for antibodies specific for rhDkk-1 protein and washed three times with serum-free DMEM and placed in a sterile Petri dish containing about 20 mL of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 mL 0.17 M ammonium chloride and placed on ice for several minutes. Then 5 mL of 20% bovine fetal serum is added and the cells pelleted by low-speed centrifugation. The cells are then resuspended in 10 mL DMEM and mixed with mid-log phase myeloma cells in serum-free DMEM to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES, pH 8.1, at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the rhDkk-1 protein. One hundred µL of supernatant from each well is added to a corresponding well on a screening plate and incubated for 1 hour at room temperature. After incubation, each well is washed three times with water and 100 µL of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 µL of 1 M HCl is added to stop the reaction and the absorbance of the wells is measured at 490 nm. Cultures that have an absorbance greater than the control wells are removed to two $cm^2$ culture dishes, with the addition of normal mouse spleen cells in HAT medium. After a further three days, the cultures are re-screened as above and those that are positive are cloned by limiting dilution. The cells in each two $cm^2$ culture dish are counted and the cell concentration adjusted to $1 \times 10^5$ cells per mL. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 cm² cultures and provided with normal mouse spleen cells. This cloning procedure is repeated until stable antibody producing hybridomas are obtained. The stable hybridomas are progressively expanded to larger culture dishes to provide stocks of the cells.

Production of ascites fluid is performed by injecting intraperitoneally 0.5 mL of pristane into female mice to prime the mice for ascites production. After 10 to 60 days, $4.5 \times 10^6$ cells are injected intraperitoneally into each mouse and ascites fluid is harvested between 7 and 14 days later.

EXAMPLE 8

In this example of a cell-based reporter assay, a signaling system in the mouse fibroblast NIH3T3 cell line is used to identify compounds which interfere with binding of rhDkk-1 protein to human LRP5. The signaling system is based on Wnt signaling using a reporter gene under the control of an LEF-1-responsive promoter (Boyden et al., N. Eng. J. Med. 346: 1513-1521 (2002); Mao et al., Mol. Cell 7: 801-809 (2001); Hsu et al., Mol. Cell. Biol. 18: 4807-4818 (1998)).

Expression plasmids encoding LEF-1 protein, Wnt-1 protein, and LRP5 are constitutively expressed from a cytomegalovirus (CMV) promoter, and the reporter gene luciferase under the control of an LEF-1 responsive promoter are disclosed in Boyden et al., supra; Mao et al., supra; Hsu et al., supra. rhDkk-1 is also constitutively expressed from a CMV promoter. Expression plasmid pcDNA3.1/Dkk-1/Myc-His-direct14 is used to express rhDkk-1.

NIH3T3 cells are cultured at 37° C. in Dulbecco's modified Eagle medium supplemented with 5% fetal bovine serum in a 5% $CO_2$ atmosphere. Transient transfections are performed by any transfection method known in the art including, but not limited to, the DEAE-dextran-chloroquine procedure, CaCl precipitation procedure, electroporation, FuGENE (Roche Applied Sciences), and LIPOFECTIN (Invitrogen) procedure. As a control for efficiency of transfection a β-galactosidase control expression plasmid is included in the transfections.

Plasmids encoding LEF-1 protein, the luciferase as the reporter gene operably linked to the LEF-1 responsive promoter, and green fluorescent protein are transfected into NIH3T3 cells seeded in 24-well plates at about $5 \times 10^4$ cells/well. Plasmids encoding LRP5, Wnt-1, and rhDkk-1 are also transfected into the cells. The total amount of DNA transfected is preferably about 0.5 µg per well. After transfection, the cells are incubated in medium containing the analyte to be tested for its ability to interfere with binding of the rhDkk-1 protein to LRP5. Controls without the analyte are routinely performed. After about 24 hours post-transfection, the cells are lysed and the levels of luciferase activity and green fluorescent protein are measured (Li et al. EMBO J. 18: 4233-4240 (1999); Yuan et al., J. Biol. Chem. 274: 30419-30423 (1999)). The luciferase activity is normalized according to the green fluorescent protein level to account for variations in the efficiency of transfection.

An increase in luciferase activity in transfected cells incubated with a particular analyte relative to controls which do not contain the analyte indicates that the analyte interferes with the inhibitory effect of rhDkk-1 on Wnt-1 signaling. Analytes which are identified in the above assay as being capable of interfering with the binding of the rhDkk-1 protein to LRP5 are candidates for further evaluation on their ability to stimulate bone formation in vivo or induce pluripotent cells to differentiate along an osteoblastic linage.

EXAMPLE 9

This examples describes a cell-binding method for identifying analytes which interfere with the ability of rhDkk-1 protein to bind a Dkk receptor on the surface of a cell. To identify interfering analytes, recombinant cells, which express LRP5 on the surface, are incubated in medium containing labeled rhDkk-1 protein. The cells are then evaluated for bound rhDkk-1 protein HEK293T cells are transfected with the LRP5 expression vector in which the human LRP5 is constitutively expressed from a cytomegalovirus (CMV) promoter. The LRP5 expression vector comprises the human LRP5 cDNA cloned into the pcDNA3 expression vector (Invitrogen) as taught in Gong et al., Cell 107: 513-523 (2001). The labeled rhDkk-1 is a rhDkk-1-AP fusion polypeptide which is provided in conditioned medium produced by transient transfection of HEK293T cells with pcDNA3.1/rhDkk-1/Myc-His-direct14 in which the alkaline phosphatase (human placental alkaline phosphatase) gene is cloned in frame at the 3' end of the rhDkk-1 cDNA in pcDNA3.1/rhDkk-1/Myc-His-direct14.

The FuGENE transfection protocol (Roche Applied Sciences) is used according to the manufacturer's instructions. Cells are plated the day before the transfection at a density to give about 50-80% confluence on the day of the transfection. About $1-3 \times 10^5$ cells in 2 mL of Dulbecco's modified Eagle's medium containing 5% fetal calf serum or 10% horse serum in a 35 mm culture dish (or 6-well plate) will achieve this density after overnight incubation at 37° C. In a small sterile tube, add sufficient serum-free medium as diluent for FuGENE 6 Transfection Reagent, to a total volume of 100 µL. About 3 to 6 µL of FuGENE 6 Reagent is added directly into this medium. Tap gently to mix. About 1-2 µg of DNA (LRP5 expression vector) solution (about 0.02-2.0 µg/µL) is added to the prediluted FuGENE 6 Reagent above. Use a total volume of DNA solution between 0.5-50 µL. Gently tap the tube to mix the contents. Incubate for a minimum of about 15 minutes at room temperature. The complex mixture is added to the cells dropwise and distributed around the well. The cells are returned to the incubator and incubated for 48 hours. After 48 hours, the cell binding assay is performed.

The medium is removed from the cells and medium containing rhDkk-1-AP fusion polypeptide and an analyte to be tested for interfering with binding of rhDkk-1 protein to LRP5 is added to the cells. Controls consist of medium containing rhDkk-1-AP only, medium containing the analyte only, and medium containing neither rhDkk-1-AP or the analyte. Detection of rhDkk-1-AP fusion polypeptide bound to LRP5 on the cell surface is by measuring alkaline phosphatase activity on the cell surface. This can be done by staining the cells with FAST RED reagent (Roche Applied Sciences). Cells with rhDkk-1-AP bound to LRP5 on the surface stain red with the reagent. A decrease in alkaline phosphatase activity in wells containing a mixture of the rhDkk-1-AP fusion protein and an analyte compared to controls containing the rhDkk-1-AP fusion protein without the analyte indicates that the analyte interferes with the binding of Dkk-1 to LRP5.

EXAMPLE 10

This example illustrates an osteoblast differentiation assay for identifying analytes which interferes with Dkk-1 protein inhibition of differentiation of pluripotent mesenchymal cells along the osteoblastic lineage in vitro.

Katagiri et al., J. Cell Biol. 127: 1755-1766 (1994) and Yamaguchi et al., Biochem. Biophys. Res. Commun. 220:

366-371 (1996) have shown that adding exogenous growth factors to pluripotent marrow stromal cells induces the cells along an osteoblastic lineage. Gong et al. (Cell 107: 513-523 (2001) show that adding 300 ng/mL of BMP2 to the pluripotent mesenchymal cells C3H10T1/2 and ST2 results in expression of the osteoblastic markers alkaline phosphatase (ALP), Bglap, and Runx2. Gong et al. further show that ALP activity can be induced in C3H10T1/2 and ST2 cells by transfecting the cells with vectors expressing LRP5 and Wnt and that ALP activity can be induced in ST2 cells that are stably expressing LRP5 by transfecting the cells with a vector expressing Wnt. Thus, the Wnt signaling pathway is involved in differentiation of pluripotent cells along an osteoblast lineage. Therefore, because Dkk-1 can inhibit the Wnt signaling pathway by binding LRP5, the osteoblast differentiation assay of Gong et al. can be adapted to an assay for identifying analytes which inhibit or suppress Dkk-1 inhibition of osteoblast differentiation.

The LRP5 expression vector comprising the human LRP5 cDNA cloned into the pcDNA3 expression vector and the Wnt expression vector comprising the Wnt3 cDNA cloned into the pcDNA3 vector are constructed as taught in Gong et al., Cell 107: 513-523 (2001). Expression plasmid pcDNA3.1/Dkk-1/Myc-His-direct14 is used to express rhDkk-1.

C3H10T1/2 or ST2 cell lines are cultured in α-MEM and RPMI medium, respectively, supplemented with 10% heat-inactivated fetal bovine serum at 37° C. in a 5% $CO_2$ atmosphere. For treatment or transient transfection, cells are plated at $2 \times 10^4/cm^2$ and 24 hr later, treatment or transfections were carried out as indicated below.

Cells are plated in 24 well plates and transiently transfected with all three constructs (about 1 µg/construct) using FuGENE 6. When required, transfection controls are used which comprise the empty pcDNA3 vector. ST2 stably transfected cell lines are maintained in the corresponding culture medium supplemented with G418 (500 µg/mL). About sixteen hours after transfection, the cells are washed, cultured in media containing 2% fetal bovine serum, and cultured either with or without a test analyte for an additional 48 hours.

ALP activity is determined in cell lysates by the Alkaline Phosphatase Opt kit (Roche Molecular Biochemicals). Cell lysates are analyzed for protein content by using the micro-BCA Assay kit (Pierce) and ALP activity is normalized for total protein concentration.

ALP activity detected in the presence of a test analyte indicates that the analyte interferes with binding of the rhDkk-1 protein to the LRP5 receptor which allows Wnt to induce differentiation along the osteoblast lineage. Conversely, the absence of ALP activity indicates that the analyte does not interfere with binding of the rhDkk-1 protein to LRP5 and there is no Wnt induced differentiation along the osteoblast lineage.

EXAMPLE 11

This example provides a cell-based assay for identifying analytes that interfere with binding between Dkk-1 and LRP5 using rhDkk-1 labeled with the lanthanide europium.

Standard cell culture medium was Dulbecco's modified Eagle's medium (DMEM) containing 10% fetal bovine serum (FBS) and penicillin/streptomycin (Gibco BRL, Gaithersburg, Md.). HEK 293 cells overexpressing human LRP5 were generated by transfecting plasmid pcDNA5/FRT (Invitrogen, La Jolla, Calif.) containing DNA encoding the human LRP5 operably linked to the CMV promoter into HEK-293 cells using lipofection, (FUGENE 6, Roche, Indianapolis, Ind.). Recombinant cells stably transfected with DNA encoding LRP5 were selected with hygromycin (100 µg/mL).

DNA encoding Dkk-1 adjacent to and in frame to a nucleotide sequence encoding polyhistidine was inserted into a baculovirus vector (pFastbac-1, Invitrogen). Baculovirus-susceptible insect cells were infected with the recombinant baculovirus vector to produce RhDkk-1 comprising a polyhistidine sequence at the carboxy terminus. The polyhistidine-tagged RhDkk-1 was purified using nickel column chromatography and labeled with europium chelate N1-isothiocyanate (Perkin Elmer, Boston, Mass.). Characterization of the labeled RhDkk-1 protein (Eu-rhDkk-1) indicated a labeling stoichiometry of about 9 Eu molecules per protein.

The rhDkk-1-LRP5 binding assays were carried out as follows. The recombinant HEK 293 cells stably overexpressing human LRP5 were plated into the wells of white/white, 384-well, PDL plates (BD Biosciences, San Jose, Calif.). Each well contained about 10,000 cells and 30 µL of medium containing 2.5% FBS. The next day, to each well, 250 nL of an analyte was added (high concentration copy, CyBi Disk) for final a concentration of about 30 µM. Next, 5 µL of Eu-rhDkk-1 (1 nM) was added to each of the wells (CyBi Well, 0.1 nM final concentration). After incubating at 37° C. for 30 minutes, the wells were washed four times each with a wash solution (Tris-buffered saline, pH 8.0) containing 0.02% Tween-20). After the final wash, 20 µL of Enhancement Solution (Perkin Elmer) was added to each of the wells. After incubating the wells in Enhancement Solution for 30 minutes at room temperature, the wells were vortexed and the time resolved fluorescence from the wells read using the LEAD-SEEKER, a CCD-based optical imaging instrument that can measure fluorescence (Amersham Biosciences, Piscataway, N.J.).

To determine whether an analyte's inhibitory effect on the binding of rhDkk-1 to human LRP5 is specific or non-specific, counterscreens were performed using either a wheat germ agglutinin-biotin/steptavidin (WGA) assay or a human TNFα assay in the same recombinant cells overexpressing the human LRP5. The WGA assay was performed with the above recombinant HEK 293 cells incubated with the analyte at a concentration of 15 µM and 2 mg/mL wheat germ agglutinin linked to biotin (WGA-biotin; Biomeda Corp., Foster City, Calif.) and 0.1 mg/mL streptavidin labeled with europium (Eu-streptavidin; Perkin Elmer) instead of the Eu-rhDkk-1. The amount of the WGA-biotin/Eu-streptavidin complex bound in the presence and absence of the analytes was measured. The TNFα assay was performed as above except that the recombinant HEK 293 cells were incubated with the analyte at a concentration of 15 µM and the TNFα labeled with europium (Eu-TNFα; Perkin Elmer; final concentration 0.1 nM) instead of Eu-rhDkk-1. The amount of TNFα bound to the cells in the presence and absence of the analytes was measured.

In the absence of an analyte, Eu-rhDkk-1 showed a binding affinity of about 1 nM. In a competition assay between rhDkk-1 and the Eu-rhDkk-1 for binding to human LRP5, the rhDkk-1 had an $IC_{50}$ of about 0.2 nM. The results of the above assay performed with several analytes are shown in Table 1. Table 1 shows that the assay identified several analytes which appeared to have an inhibitory effect on the binding of rhDkk-1 to human LRP5.

TABLE 1

| | rhDkk1/LRP5 | Percent Inhibition of Binding at 15 µM | |
|---|---|---|---|
| Analyte | IC$_{50}$ (µM) | WGA | TNFα |
| A | 4.6 | 0% | 0% |
| B | About 5 | 0% | 7% |
| C | 5.2 | 0% | 0% |
| D | 8.9 | 42% | 2% |
| E | 9.6 | 8% | 9% |
| F | 17.1 | 5% | 26% |
| G | 22.0 | 0% | 9% |
| H | Less than 5 | 78% | 100% |
| I | Less than 5 | 100% | 100% |
| J | 12.0 | 59% | 100% |
| K | Greater than 45 | 5% | 0% |

Table 1 shows that analytes A through G appear to have an inhibitory effect on the binding of rhDkk-1 to human LRP5. The inhibitory effect appears to be specific for several of the analytes as shown by the counterscreens using WGA and TNFα. Analytes H through J appear to have an inhibitory effect on binding of rhDkk-1 to human LRP5; however, the effect is non-specific as shown by the non-specific activity in both the WGA and TNFα counterscreens. Compound K is an example of an analyte which appears to have no inhibitory effect either on the binding of rhDkk-1 to human LRP5 or in the WGA and TNFa counterscreens.

EXAMPLE 12

This example provides a cell-based assay for identifying analytes that interfere with binding between Dkk-1 and LRP5 using a fusion protein comprising the rhDkk-1 fused to the Green fluorescence protein.

Recombinant cells stably transfected with DNA encoding LRP5 were produced as previously described.

Fusion proteins comprising the rhDkk-1 fused to the Green fluorescence protein (GFP) were prepared as follows. DNA encoding rhDkk-1 was cloned in-frame with DNA encoding the GFP using expression plasmid pEGFP-N2 (Clontech, Palo Alto, Calif.) to produce a DNA encoding the fusion protein rhDkk-1-GFP. An expression plasmid encoding the rhDkk-1-GFP fusion protein was transfected in HEK 293 cells. The transfected cells were incubated at 37° C. in 5% CO$_2$. Seventy-two hours later, medium was removed from the cells, sterile filtered, and supplemented with 20 mM Hepes-buffer (pH 7.5) to produce conditioned medium.

The rhDkk-1-GFP fusion protein-LRP5 binding assays were as follows. Recombinant HEK-293 cells stably overexpressing human LRP5 were plated into the wells of a 384-well tissue culture plate (Corning) at a concentration of about 6,000 cells/well. Each well contained 45 µL of phenol red-free DMEM containing 2.5% FBS. To each well, an analyte was added to give a final concentration of 15 µM. A minute later, 5 µL of conditioned medium containing rhDkk-1-GFP and 10 µM DRAQ5 nuclear stain is added to each well and the wells incubated at 37° C. for 25 minutes. Imaging and evaluation of rhDkk-1-GFP fusion protein binding to the recombinant cells overexpressing LRP5 was determined using an INCell 3000 imager (Amersham, Piscataway, N.J.).

In a competition assay between rhDkk-1 and the rhDkk-1-GFP fusion protein for binding to LRP5, the rhDkk-1 had an IC$_{50}$ of about 1 nM. The results of the above assay performed with several analytes are shown in Table 2. Table 2 shows that in the above assay, analytes D, F, and G were able to inhibit binding of rhDkk-1-GFP fusion protein to human LRP5 on the surface of the recombinant cells overexpressing LRP5.

TABLE 2

| Analyte | Percent Inhibition of Binding at 15 µM |
|---|---|
| A | 19% |
| B | NT |
| C | NT |
| D | 84% |
| E | NT |
| F | 80% |
| G | 68% |

EXAMPLE 13

This examples provides a cell-based functional assay for determining whether an analyte can activate the Wnt pathway by interfering with the binding of Dkk-1 to LRP5.

Recombinant cells stably transfected with DNA encoding LRP5 were produced as previously described.

Cells were seeded in DMEM containing 2.5% FBS (80 µL) into the wells of a multi-well tissue culture plate at a concentration of about 50,000/cm$^2$ and transfected with 3 ng pTOP-FLASH (a plasmid vector comprising the luciferase gene operably linked to the thymidine kinase minimal promoter adjacent to TCF/LEF binding site; Upstate Biotechnology, Lake Saranac, N.Y.) and 0.08 ng pTK-renilla (Promega Corp., Madison, Wis.) using FUGENE 6 (Roche, Indianapolis, Ind.) in OPTIMEM medium (Gibco BRL). The plasmid pTK-renilla was included for normalizing transfection efficiency.

Twenty-four hours post-transfection, an analyte was added to each of the wells (final concentration ranging from about 2.5 to 23 µM). Afterwards, rhDkk1 and a Wnt-ligand (Wnt3A) were added to each of the wells. Wnt ligand was added as 1 ug purified Wnt ligand or 100 uL of conditioned medium obtained from cells transfected with a plasmid encoding Wnt ligand (for example, American Type Culture Collection CRL-2647), or by transfecting the above recombinant HEK293 cells with 10 ng of a plasmid comprising DNA encoding the Wnt ligand. RhDkk-1 was provided as 2 µg purified rhDkk-1 protein or 100 µL of conditioned medium obtained from cells transfected with 700 ng of a plasmid encoding rhDkk-1, or by transfecting the above recombinant HEK293 cells with 10 ng of a plasmid comprising DNA encoding rhDkk-1. About 6 to 48 hours after the analytes had been added to the wells, the recombinant cells were lysed by adding 20 µL of 1× Passive Lysis buffer (Promega). Luciferase activities were measured in a VICTOR3 plate reader (Perkin Elmer).

An increase in luciferase expression indicates that the analyte being tested interferes with binding of rhDkk-1 to LRP5. The interference enables the LRP5 to interact with the Wnt ligand and Frizzled on the cell membrane, which in turn recruits Axin and disheveled to the inner cell membrane, which in a series of intracellular events causes β-catenin to accumulate in the cytoplasm. The β-catenin then translocates to the nucleus where it interacts TCF transcription factors to activate transcription of the luciferase gene provided by pTOPFLASH. As shown in table 3, analytes B, D, and F appeared to inhibit rhDkk-1 inhibition of the Wnt signaling pathway.

TABLE 3

| Analyte | Percent Inhibition of Dkk1 Inhibition of Wnt Signaling (mean) |
|---|---|
| A | 6% |
| B | 34% |
| C | NT |
| D | 12% |
| E | 0% |
| F | 26% |
| G | 9% |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. An isolated and purified rhesus dickkopf-1 (rhDkk-1) polypeptide comprising the sequence of amino acids as set forth in SEQ ID NO:2.

2. A method for determining whether an analyte is an antagonist of Dickkopf1 (Dkk-1) comprising:
   (a) providing a polypeptide comprising the extracellular domain of a Dkk-1 receptor;
   (b) contacting the polypeptide with a rhesus monkey Dkk-1 (rhDkk-1) polypeptide comprising the sequence of amino acids as set forth in SEQ ID NO:2 and the analyte; and
   (c) determining whether binding of the rhDkk-1 to the polypeptide is decreased in the presence of the analyte, wherein a decrease in the binding indicates that the analyte is an rhDkk-1 antagonist.

3. The method of claim 2, wherein the Dkk-1 receptor is low-density lipoprotein receptor related protein 5 (LRP5) or low density lipoprotein receptor related protein 6 (LRP6).

4. The method of claim 2, wherein the Dkk-1 receptor is kremen1 or kremen2.

5. The method of claim 2 wherein the rhDkk-1 is labeled.

6. The method of claim 2 wherein the rhDkk-1 is a fusion protein.

* * * * *

SEQUENCE LISTING

<160> NUMBER OF SEQ ID NOS: 22

<210> SEQ ID NO 1
<211> LENGTH: 801
<212> TYPE: DNA
<213> ORGANISM: Macaca mulatta

<400> SEQUENCE: 1

```
atgatggctc tgggcgcagc aggagctgcc cgggtcttgg tcgcgctggt agcggcggct      60
cttggcggcc accctctgct gggagtgagc gccaccttga actcggttct caattccaac     120
gcgatcaaga acctgccccc accgctgggc ggcgctgcgg ggcacccagg ctctgcagtc     180
agcgccgcgc aggaattct  gtacccgggc gggaataagt accagaccat tgacaactac     240
cagccgtacc cgtgcgcaga ggatgaggag tgcggcactg atgagtactg cgctagtccc     300
acccgcggag gggacgcggg cgtgcaaatc tgtctcgcct gcaggaagcg ccgaaaacgc     360
tgcatgcgtc acgctatgtg ctgccccggg aattactgca aaaatggaat atgtgtgtct     420
tctgatcaaa ataatttccg aggggaaatt gaggaaacca ttactgaaag ctttggtaat     480
gatcatagca ctttggatgg gtattccaga agaacaacat tgtcttcaaa aatgtatcac     540
agcaaaggac aagaaggttc tgtgtgtctc cggtcatcag actgtgccac aggactgtgt     600
tgtgctagac acttctggtc caagatctgt aaacctgtcc tcaaagaagg tcaagtgtgt     660
accaagcata gaagaaaagg ctctcatggg ctagaaatat tccagcgttg ttactgcgga     720
gaaggtctgt cttgccggat acagaaagat caccatcaag ccagtaattc ttctaggctt     780
cacacttgtc agagacacta a                                               801
```

<210> SEQ ID NO 2
<211> LENGTH: 266
<212> TYPE: PRT
<213> ORGANISM: Macaca mulatta

<400> SEQUENCE: 2

```
Met Met Ala Leu Gly Ala Ala Gly Ala Ala Arg Val Leu Val Ala Leu
 1               5                  10                  15

Val Ala Ala Ala Leu Gly Gly His Pro Leu Leu Gly Val Ser Ala Thr
             20                  25                  30

Leu Asn Ser Val Leu Asn Ser Asn Ala Ile Lys Asn Leu Pro Pro Pro
         35                  40                  45

Leu Gly Gly Ala Ala Gly His Pro Gly Ser Ala Val Ser Ala Ala Pro
     50                  55                  60

Gly Ile Leu Tyr Pro Gly Gly Asn Lys Tyr Gln Thr Ile Asp Asn Tyr
```

```
                65                  70                  75                  80
Gln Pro Tyr Pro Cys Ala Glu Asp Glu Cys Gly Thr Asp Glu Tyr
                    85                  90                  95
Cys Ala Ser Pro Thr Arg Gly Gly Asp Ala Gly Val Gln Ile Cys Leu
                100                 105                 110
Ala Cys Arg Lys Arg Arg Lys Arg Cys Met Arg His Ala Met Cys Cys
            115                 120                 125
Pro Gly Asn Tyr Cys Lys Asn Gly Ile Cys Val Ser Ser Asp Gln Asn
    130                 135                 140
Asn Phe Arg Gly Glu Ile Glu Glu Thr Ile Thr Glu Ser Phe Gly Asn
145                 150                 155                 160
Asp His Ser Thr Leu Asp Gly Tyr Ser Arg Arg Thr Thr Leu Ser Ser
                165                 170                 175
Lys Met Tyr His Ser Lys Gly Gln Glu Gly Ser Val Cys Leu Arg Ser
                180                 185                 190
Ser Asp Cys Ala Thr Gly Leu Cys Cys Ala Arg His Phe Trp Ser Lys
            195                 200                 205
Ile Cys Lys Pro Val Leu Lys Glu Gly Gln Val Cys Thr Lys His Arg
    210                 215                 220
Arg Lys Gly Ser His Gly Leu Glu Ile Phe Gln Arg Cys Tyr Cys Gly
225                 230                 235                 240
Glu Gly Leu Ser Cys Arg Ile Gln Lys Asp His His Gln Ala Ser Asn
                245                 250                 255
Ser Ser Arg Leu His Thr Cys Gln Arg His
                260                 265

<210> SEQ ID NO 3
<211> LENGTH: 21
<212> TYPE: DNA
<213> ORGANISM: Artificial Sequence
<220> FEATURE:
<223> OTHER INFORMATION: Rat Dkk-1 forward primer

<400> SEQUENCE: 3
ggtctggctt gcaggataca g                                      21

<210> SEQ ID NO 4
<211> LENGTH: 23
<212> TYPE: DNA
<213> ORGANISM: Artificial Sequence
<220> FEATURE:
<223> OTHER INFORMATION: Rat Dkk-1 reverse primer

<400> SEQUENCE: 4
tggttttagt gtctctggca ggt                                    23

<210> SEQ ID NO 5
<211> LENGTH: 26
<212> TYPE: DNA
<213> ORGANISM: Artificial Sequence
<220> FEATURE:
<223> OTHER INFORMATION: Rat Dkk-1 Probe

<400> SEQUENCE: 5
ccatcaaacc agcaattctt ccaggc                                 26

<210> SEQ ID NO 6
<211> LENGTH: 26
<212> TYPE: DNA
<213> ORGANISM: Artificial Sequence
```

```
<220> FEATURE:
<223> OTHER INFORMATION: Human Dkk-1 forward primer

<400> SEQUENCE: 6
agtaccagac cattgacaac taccag                                            26

<210> SEQ ID NO 7
<211> LENGTH: 23
<212> TYPE: DNA
<213> ORGANISM: Artificial Sequence
<220> FEATURE:
<223> OTHER INFORMATION: Human Dkk-1 reverse primer

<400> SEQUENCE: 7
gggactagcg cagtactcat cag                                               23

<210> SEQ ID NO 8
<211> LENGTH: 22
<212> TYPE: DNA
<213> ORGANISM: Artificial Sequence
<220> FEATURE:
<223> OTHER INFORMATION: Human Dkk-1 probe

<400> SEQUENCE: 8
tacccgtgcg cagaggacga gg                                                22

<210> SEQ ID NO 9
<211> LENGTH: 26
<212> TYPE: DNA
<213> ORGANISM: Artificial Sequence
<220> FEATURE:
<223> OTHER INFORMATION: Rhesus Monkey Dkk-1 forward primer

<400> SEQUENCE: 9
gaaggtcaag tgtgtaccaa gcatag                                            26

<210> SEQ ID NO 10
<211> LENGTH: 27
<212> TYPE: DNA
<213> ORGANISM: Artificial Sequence
<220> FEATURE:
<223> OTHER INFORMATION: Rhesus Monkey Dkk-1 reverse primer

<400> SEQUENCE: 10
aagtgtgaag cctagaagaa ttactgg                                           27

<210> SEQ ID NO 11
<211> LENGTH: 29
<212> TYPE: DNA
<213> ORGANISM: Artificial Sequence
<220> FEATURE:
<223> OTHER INFORMATION: Rhesus Monkey Dkk-1 probe

<400> SEQUENCE: 11
ttgatggtga tctttctgta tccggcaag                                         29

<210> SEQ ID NO 12
<211> LENGTH: 26
<212> TYPE: DNA
<213> ORGANISM: Artificial Sequence
<220> FEATURE:
<223> OTHER INFORMATION: 5'h Dkk-1 Forward

<400> SEQUENCE: 12
tctccctctt gagtccttct gagatg                                            26
```

<210> SEQ ID NO 13
<211> LENGTH: 24
<212> TYPE: DNA
<213> ORGANISM: Artificial Sequence
<220> FEATURE:
<223> OTHER INFORMATION: 5'h Dkk-1 Reverse

<400> SEQUENCE: 13
cgttggaatt gagaaccgag ttca                                             24

<210> SEQ ID NO 14
<211> LENGTH: 25
<212> TYPE: DNA
<213> ORGANISM: Artificial Sequence
<220> FEATURE:
<223> OTHER INFORMATION: 3'h Dkk-1 Forward

<400> SEQUENCE: 14
gtcatcagac tgtgcctcag gattg                                            25

<210> SEQ ID NO 15
<211> LENGTH: 26
<212> TYPE: DNA
<213> ORGANISM: Artificial Sequence
<220> FEATURE:
<223> OTHER INFORMATION: 3'h Dkk-1 Reverse

<400> SEQUENCE: 15
gagttcactg catttggata gctggt                                           26

<210> SEQ ID NO 16
<211> LENGTH: 24
<212> TYPE: DNA
<213> ORGANISM: Artificial Sequence
<220> FEATURE:
<223> OTHER INFORMATION: h Dkk-1 R3

<400> SEQUENCE: 16
gcactgatga gtactgcgct agtc                                             24

<210> SEQ ID NO 17
<211> LENGTH: 20
<212> TYPE: DNA
<213> ORGANISM: Artificial Sequence
<220> FEATURE:
<223> OTHER INFORMATION: h Dkk-1 F3

<400> SEQUENCE: 17
cacatagcgt gacgcatgca                                                  20

<210> SEQ ID NO 18
<211> LENGTH: 35
<212> TYPE: DNA
<213> ORGANISM: Artificial Sequence
<220> FEATURE:
<223> OTHER INFORMATION: rh Dkk-1 Eco RI-F

<400> SEQUENCE: 18
cggaattcac catgatggct ctgggcgcag cagga                                 35

<210> SEQ ID NO 19
<211> LENGTH: 38
<212> TYPE: DNA
<213> ORGANISM: Artificial Sequence
<220> FEATURE:
<223> OTHER INFORMATION: h Dkk-1 Eco RI-R

<400> SEQUENCE: 19
cggaattcgt gtctctgaca agtgtgaagc ctagaaga                              38

<210> SEQ ID NO 20
<211> LENGTH: 801
<212> TYPE: DNA
<213> ORGANISM: Homo sapiens

<400> SEQUENCE: 20
atgatggctc tgggcgcagc gggagctacc cgggtctttg tcgcgatggt agcggcggct        60
ctcggcggcc accctctgct gggagtgagc gccaccttga actcggttct caattccaac      120
gctatcaaga acctgccccc accgctgggc ggcgctgcgg ggcacccagg ctctgcagtc      180
agcgccgcgc cgggaatcct gtacccgggc gggaataagt accagaccat tgacaactac      240
cagccgtacc cgtgcgcaga ggacgaggag tgcggcactg atgagtactg cgctagtccc      300
acccgcggag gggacgcggg cgtgcaaatc tgtctcgcct gcaggaagcg ccgaaaacgc      360
tgcatgcgtc acgctatgtg ctgccccggg aattactgca aaaatggaat atgtgtgtct      420
tctgatcaaa atcatttccg aggagaaatt gaggaaacca tcactgaaag ctttggtaat      480
gatcatagca ccttggatgg gtattccaga agaaccacct tgtcttcaaa aatgtatcac      540
accaaaggac aagaaggttc tgtttgtctc cggtcatcag actgtgcctc aggattgtgt      600
tgtgctagac acttctggtc caagatctgt aaacctgtcc tgaaagaagg tcaagtgtgt      660
accaagcata ggagaaaagg ctctcatgga ctagaaatat tccagcgttg ttactgtgga      720
gaaggtctgt cttgccggat acagaaagat caccatcaag ccagtaattc ttctaggctt      780
cacacttgtc agagacacta a                                                801

<210> SEQ ID NO 21
<211> LENGTH: 265
<212> TYPE: PRT
<213> ORGANISM: Homo sapiens

<400> SEQUENCE: 21

Met Met Ala Leu Gly Ala Ala Gly Ala Thr Arg Val Phe Val Ala Met Val
1               5                   10                  15

Ala Ala Ala Leu Gly Gly His Pro Leu Leu Gly Val Ser Ala Thr Leu
                20                  25                  30

Asn Ser Val Leu Asn Ser Asn Ala Ile Lys Asn Leu Pro Pro Pro Leu
            35                  40                  45

Gly Gly Ala Ala Gly His Pro Gly Ser Ala Val Ser Ala Ala Pro Gly
        50                  55                  60

Ile Leu Tyr Pro Gly Gly Asn Lys Tyr Gln Thr Ile Asp Asn Tyr Gln
65                  70                  75                  80

Pro Tyr Pro Cys Ala Glu Asp Glu Glu Cys Gly Thr Asp Glu Tyr Cys
                85                  90                  95

Ala Ser Pro Thr Arg Gly Gly Asp Ala Gly Val Gln Ile Cys Leu Ala
            100                 105                 110

Cys Arg Lys Arg Arg Lys Arg Cys Met Arg His Ala Met Cys Cys Pro
        115                 120                 125

Gly Asn Tyr Cys Lys Asn Gly Ile Cys Val Ser Ser Asp Gln Asn His
    130                 135                 140

Phe Arg Gly Glu Ile Glu Glu Thr Ile Thr Glu Ser Phe Gly Asn Asp
145                 150                 155                 160

-continued

```
His Ser Thr Leu Asp Gly Tyr Ser Arg Arg Thr Leu Ser Ser Lys
            165                 170                 175

Met Tyr His Thr Lys Gly Gln Glu Gly Ser Val Cys Leu Arg Ser Ser
            180                 185                 190

Asp Cys Ala Ser Gly Leu Cys Cys Ala Arg His Phe Trp Ser Lys Ile
            195                 200                 205

Cys Lys Pro Val Leu Lys Glu Gly Gln Val Cys Thr Lys His Arg Arg
    210                 215                 220

Lys Gly Ser His Gly Leu Glu Ile Phe Gln Arg Cys Tyr Cys Gly Glu
225                 230                 235                 240

Gly Leu Ser Cys Arg Ile Gln Lys Asp His His Gln Ala Ser Asn Ser
                245                 250                 255

Ser Arg Leu His Thr Cys Gln Arg His
            260                 265

<210> SEQ ID NO 22
<211> LENGTH: 272
<212> TYPE: PRT
<213> ORGANISM: Mus musculus

<400> SEQUENCE: 22

Met Met Val Val Cys Ala Pro Ala Val Arg Phe Leu Ala Val Phe
  1               5                  10                  15

Thr Met Met Ala Leu Cys Ser Leu Pro Leu Leu Gly Ala Ser Ala Thr
            20                  25                  30

Leu Asn Ser Val Leu Ile Asn Ser Asn Ala Ile Lys Asn Leu Pro Pro
        35                  40                  45

Pro Leu Gly Gly Ala Gly Gly Gln Pro Gly Ser Ala Val Ser Val Ala
    50                  55                  60

Pro Gly Val Leu Tyr Glu Gly Gly Asn Lys Tyr Gln Thr Leu Asp Asn
65                  70                  75                  80

Tyr Gln Pro Tyr Pro Cys Ala Glu Asp Glu Glu Cys Gly Ser Asp Glu
                85                  90                  95

Tyr Cys Ser Ser Pro Ser Arg Gly Ala Ala Gly Val Gly Gly Val Gln
            100                 105                 110

Ile Cys Leu Ala Cys Arg Lys Arg Arg Lys Arg Cys Met Thr His Ala
        115                 120                 125

Met Cys Cys Pro Gly Asn Tyr Cys Lys Asn Gly Ile Cys Met Pro Ser
    130                 135                 140

Asp His Ser His Phe Pro Arg Gly Glu Ile Glu Ser Ile Ile Glu
145                 150                 155                 160

Asn Leu Gly Asn Asp His Asn Ala Ala Ala Gly Asp Gly Tyr Pro Arg
                165                 170                 175

Arg Thr Thr Leu Thr Ser Lys Ile Tyr His Thr Lys Gly Gln Glu Gly
            180                 185                 190

Ser Val Cys Leu Arg Ser Ser Asp Cys Ala Ala Gly Leu Cys Cys Ala
        195                 200                 205

Arg His Phe Trp Ser Lys Ile Cys Lys Pro Val Leu Lys Glu Gly Gln
    210                 215                 220

Val Cys Thr Lys His Lys Arg Lys Gly Ser His Gly Leu Glu Ile Phe
225                 230                 235                 240
```

-continued

```
Gln Arg Cys Tyr Cys Gly Glu Gly Leu Ala Cys Arg Ile Gln Lys Asp
            245                 250                 255
His His Gln Ala Ser Asn Ser Ser Arg Leu His Thr Cys Gln Arg His
            260                 265                 270
```